(12) United States Patent
Tatake et al.

(10) Patent No.: US 6,537,784 B1
(45) Date of Patent: *Mar. 25, 2003

(54) SELF-REGULATED APOPTOSIS OF INFLAMMATORY CELLS BY GENE THERAPY

(75) Inventors: Revati J. Tatake, Sandy Hook, CT (US); Steven D. Marlin, Sandy Hook, CT (US); Randall W. Barton, Farmington, CT (US)

(73) Assignee: Boehringer Ingelheim Pharmaceuticals Inc., Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/229,151

(22) Filed: Jan. 12, 1999

Related U.S. Application Data

(60) Provisional application No. 60/076,316, filed on Feb. 27, 1998.

(51) Int. Cl.[7] .......................... C12P 19/34; C12N 15/64; C12N 15/00; C12Q 1/02; C07H 21/04
(52) U.S. Cl. ........................... 435/91.1; 435/6; 435/29; 435/320.1; 435/455; 435/91.4; 536/23.1; 536/23.2; 536/24.1
(58) Field of Search .................... 435/455, 91.1, 435/91.4, 6, 29, 320.1; 536/23.1, 23.2, 24.1

(56) References Cited

U.S. PATENT DOCUMENTS

| | | |
|---|---|---|
| 5,744,304 A | 4/1998 | Munford |
| 5,792,751 A | 8/1998 | Ledley et al. |

FOREIGN PATENT DOCUMENTS

| | | |
|---|---|---|
| WO | WO 94/01139 | 1/1994 |
| WO | WO 95/10630 | 4/1995 |
| WO | WO 97/07828 | 3/1997 |
| WO | WO 98/37901 | 9/1998 |

OTHER PUBLICATIONS

Leitman, DC, et al; Identification of a Tumor Necrosis Factor–responsive Element in the Tumor Necrosis Facotr a Gene; The Journal of Biological Chemistry, 1991; 266(15) 9343:9346.

Heusel, Jonathan W. et al; Cytotoxic Lymphocytes Require Granzyme B for the Rapid Induction of DNA Fragmentation and Apoptosis in Allogeneic Target Cells, Cell, vol. 76, 977–987, XP 000676424 Mar. 25, 1994.

Chinnaiyan, Arul M., et al, Cytotoxic T–cell–derived Granzume B activates the apoptotic protease ICE–LAP3, Current Biology 1996, vol. 6, No. 7, 897–899, XP 000614645.

Anderson, Gary P.; Resolution of Chronic Inflammation By Therapeutic Induction of Apoptosis, Current Awareness, TIPS–Dec. 1996 (vol. 17), 438–442 XP 4063291A.

Takashiba, Shogo, Cloning and Characterization of Human TNFx Promoter Region, Gene 131, 1993 307–308, XP–002103473.

Rhoades, Kristina L., et al; The Regulation of the Human Tumor Necrosis Factor α Promoter Region in Macrophage, T Cell, and B Cell Lines; Journal of Biological Chemistry, vol. 267, No. 31 Issue of Nov. 5, pp. 22,102–22,107, 1992.

Bellamy, et al, Cell death in health and disease: the biology and regulation of apoptosis. Sem Cancer Biol. Feb. 1995, vol. 6, No. 1, pp. 3–16.

*Primary Examiner*—David Guzo
*Assistant Examiner*—Gerald G. Leffers, Jr.
(74) *Attorney, Agent, or Firm*—Robert P. Raymond; Susan K. Pocchiari; Mary-Ellen M. Devlin

(57) ABSTRACT

This invention relates to chimeric nucleic acids and to the therapeutic induction of apoptosis in activated inflammatory cells, or cells at a site of inflammation, by introducing into those cells the chimeric nucleic acid. The chimeric nucleic acid having at least one TNFα promoter enhancer attached to a functional copy of a TNFα promoter and further attached to at least one copy of an apoptosis-inducing gene, which is further attached to a 3'UTR. The apoptosis-inducing gene is Granzyme B. The invention also relates to methods of making and using self-regulated apoptosis chimeric nucleic acids and pharmaceutical compositions containing them for treating inflammatory diseases.

11 Claims, 18 Drawing Sheets

Chimeric Nucleic Acid (-706TNFpGB3'UTR)

*CTCGAG*tccttggaagccaagactgaaaccagcattatgagtctccgggtcagaatgaaagaagaa
ggcctgccccagtggggtctgtgaattcccggggtgatttcactccccggggctgtcccaggctt
gtccctgctaccccacccagcctttcctgaggctcaagcctgccaccaagccccagctccttct
ccccgcagggacccaaacacaggcctcaggactcaacacagcttttcctccaaccccgttttctc
tccctcaaggactcagctttctgaagcccctcccagttctagttctatcttttcctgcatcctgt
ctggaagttagaaggaaacagaccacagacctggtccccaaaagaaatggaggcaataggttttga
ggggcatggggacggggttcagcctccagggtcctacacacaaatcagtcagtggcccagaagacc
ccctcggaatcggagcagggaggatggggagtgtgaggggtatccttgatgcttgtgtgtcccca
actttccaaatccccgccccgcgatggagaagaaaccgagacagaaggtgcagggccactaccg
cttcctccagatgagctcatgggtttctccaccaaggaagttttccgctggttgaatgattctttc
cccgcctcctctcgccccagggacatataaaggcagttgttggcacacccagccagcagacgctc
cctcagc*AGATCT*ATGCAACCAATCCTGCTTCTGCTGGCCTTCCTCCTGCTGCCCAGGGCAGATGC
AATCATCGGGGACATGAGGCCAAGCCCCACTCCCGCCCCTACATGGCTTATCTTATGATCTGGGA
TCAGAAGTCTCTGAAGAGGTGCGGTGGCTTCCTGATACAAGACGACTTCGTGCTGACAGCTGCTCA
CTGTTGGGGAAGCTCCATAAATGTCACCTTGGGGGCCCACAATATCAAAGAACAGGAGCCGACCCA
GCAGTTTATCCCTGTGAAAAGACCCATCCCCCATCCAGCCTATAATCCTAAGAACTTCTCCAACGA
CATCATGCTACTGCAGCTGGAGAGAAAGGCCAAGCGGACCAGAGCTGTGCAGCCCCTCAGGCTACC
TAGCAACAAGGCCCAGGTGAAGCCAGGGCAGACATGCAGTGTGGCCGGCTGGGGGCAGACGGCCCC
CCTGGGAAAACACTCACACACACTACAAGAGGTGAAGATGACAGTGCAGGAAGATCGAAAGTGCGA
ATCTGACTTACGCCATTATTACGACAGTACCATTGAGTTGTGCGTGGGGGACCCAGAGATTAAAAA
GACTTCCTTTAAGGGGGACTCTGGAGGCCCTCTTGTGTGTAACAAGGTGGCCCAGGGGATTGTCTC
CTATGGACGAAACAATGGCATGCCTCCACGAGCCTGCACCAAAGTCTCAAGCTTTGTACACTGGAT
AAAGAAAACCATGAAACGCTACTAAG*AATTCTCTAGA*ggaggacgaacatccaaccttcccaaacg
cctccctgccccaatccctttattaccccctccttcagacaccctcaacctcttctggctcaaaa
agagaattgggggcttaggggtcggaacccaagcttagaactttaagcaacaagaccaccacttcga
aacctgggattcaggaatgtgtggcctgcacagtgaagtgctggcaaccactaagaattcaaactg
gggcctccagaactcactggggcctacagctttgatccctgacatctggaatctggagaccaggga
gcctttggttctggccagaatgctgcaggacttgagaagacctcacctagaaattgacacaagtgg
accttaggccttcctctctccagatgtttccagacttccttgagacacggagcccagccctcccca
tggagccagctccctctatttatgtttgcacttgtgattatttattatttatttattatttattta
tttacagatgaatgtatttatttgggagaccggggtatcctggggacccaatgtaggagctgcct
tggctcagacatgttttccgtgaaaacggagctgaacaataggctgttcccatgtagcccctggc
ctctgtgccttctttgattatgtttttaaaatatttatctgattaagttgtctaaacaatgctg
atttggtgaccaactgtcactcattgctgagcctctgctcccaggggagttgtgtctgtaatcgc
cctactattcagtggcgaga*TCTAGA*

Figure 12

Promoter sequence-lowercase, linker sequence-uppercase Italics, Granzyme B sequence-uppercase, TNFα3'UTR sequence -lowercase underlined

Chimeric Nucleic Acid (-1005TNFpGB3'UTR)

*CTCGAG*ggcgggggtcagggagctcctgggagatatggccacatgtagcggctctgaggaatgggt
tacaggagacctctggggagatgtgaccacagcaatgggtaggagaatgtccagggctatggaagt
cgagtatggggaccccccttaacgaagacagggccatgtagagggccccagggagtgaaagagcc
tccaggacctccaggtatggaatacaggggacgtttaagaagatatggccacacactggggccctg
agaagtgagagcttcatgaaaaaaatcagggaccccagagttccttggaagccaagactgaaacca
gcattatgagtctccgggtcagaatgaaagaagaaggcctgccccagtggggtctgtgaattcccg
ggggtgatttcactccccggggctgtcccaggcttgtccctgctaccccacccagcctttcctga
ggcctcaagcctgccaccaagcccccagctccttctcccgcagggacccaaacacaggcctcagg
actcaacacagcttttccctccaacccgttttctctccctcaaggactcagctttctgaagcccc
tcccagttctagttctatctttttcctgcatcctgtctggaagttagaaggaaacagaccacagac
ctggtccccaaaagaaatggaggcaataggttttgaggggcatggggacggggttcagcctccagg
gtcctaCacacaaatcagtcagtggcccagaagacccccctcggaatcggagcagggaggatgggg
agtgtgagggtatccttgatgcttgtgtgtccccaactttccaaatccccgcccccgcgatggag
aagaaaccgagacagaaggtgcagggcccactaccgcttcctccagatgagctcatgggtttctcc
accaaggaagttttccgctggttgaatgattctttccccgccctcctctcgccccagggacatata
aaggcagttgttggcacacccagccagcagacgctccctcagc*AGATCTA*TGCAACCAATCCTGCT
TCTGCTGGCCTTCCTCCTGCTGCCCAGGGCAGATGCAATCATCGGGGGACATGAGGCCAAGCCCCA
CTCCCGCCCCTACATGGCTTATCTTATGATCTGGGATCAGAAGTCTCTGAAGAGGTGCGGTGGCTT
CCTGATACAAGACGACTTCGTGCTGACAGCTGCTCACTGTTGGGGAAGCTCCATAAATGTCACCTT
GGGGGCCCACAATATCAAAGAACAGGAGCCGACCCAGCAGTTTATCCCTGTGAAAAGACCCATCCC
CCATCCAGCCTATAATCCTAAGAACTTCTCCAACGACATCATGCTACTGCAGCTGGAGAGAAAGGC
CAAGCGGACCAGAGCTGTGCAGCCCCTCAGGCTACCTAGCAACAAGGCCCAGGTGAAGCCAGGGCA
GACATGCAGTGTGGCCGGCTGGGGGCAGACGGCCCCCCTGGGAAAACACTCACACACACTACAAGA
GGTGAAGATGACAGTGCAGGAAGATCGAAAGTGCGAATCTGACTTACGCCATTATTACGACAGTAC
CATTGAGTTGTGCGTGGGGGACCCAGAGATTAAAAAGACTTCCTTTAAGGGGGACTCTGGAGGCCC
TCTTGTGTGTAACAAGGTGGCCCAGGGCATTGTCTCCTATGGACGAAACAATGGCATGCCTCCACG
AGCCTGCACCAAAGTCTCAAGCTTTGTACACTGGATAAAGAAAACCATGAAACGCTACTAA*GAATT
CTCTAGA*ggaggacgaacatccaaccttcccaaacgcctccctgccccaatccctttattaccc
ctccttcagacaccctcaacctcttctggctcaaaaagagaattgggggcttagggtcggaaccca
agcttagaactttaagcaacaagaccaccacttcgaaacctgggattcaggaatgtgtggcctgca
cagtgaagtgctggcaaccactaagaattcaaactggggcctccagaactcactggggcctacagc
tttgatccctgacatctggaatctggagaccagggagcctttggttctggccagaatgctgcagga
cttgagaagacctcacctagaaattgacacaagtggaccttaggccttcctctctccagatgtttc
cagacttccttgagacacggagcccagccctccccatggagccagctccctctatttatgtttgca
cttgtgattatttatttatttattattttatttatttacagatgaatgtatttatttgggagac
cggggtatcctgggggacccaatgtaggagctgccttggctcagacatgttttccgtgaaaacgga
gctgaacaataggctgttccatgtagcccctggcctctgtgccttcttttgattatgttttta
aaatatttatctgattaagttgtctaaacaatgctgatttggtgaccaactgtcactcattgctga
gcctctgctccccaggggagttgtgtctgtaatcgccctactattcagtggcgaga*TCTAGA*

Figure 13

Promoter sequence-lowercase, linker sequence-uppercase Italics, Granzyme B sequence-uppercase, TNFα3'UTR sequence -lowercase underlined

SEQUENCE LISTING

```
<160> NUMBER OF SEQ ID NOS: 15

<210> SEQ ID NO 1
<211> LENGTH: 1178
<212> TYPE: DNA
<213> ORGANISM: Human
<220> FEATURE:
<221> NAME/KEY: unsure
<222> LOCATION: 881
<223> OTHER INFORMATION: Human TNF-alpha promoter

<400> SEQUENCE: 1
ggggaagcaa aggagaagct gagaagatga aggaaaagtc agggtctgga ggggcggggg        60
tcagggagct cctgggagat atggccacat gtagcggctc tgaggaatgg gttacaggag      120
acctctgggg agatgtgacc acagcaatgg gtaggagaat gtccagggct atggaagtcg      180
```

-continued

```
agtatcgggg accccccctt aacgaagaca gggccatgta gagggcccca gggagtgaaa      240
gagcctccag gacctccagg tatggaatac aggggacgtt taagaagata tggccacaca      300
ctggggccct gagaagtgag agcttcatga aaaaaatcag gaccccagag ttccttggaa      360 gccaagact gaaaccagca ttatgagtct ccgggtcaga atgaaagaag aaggcctgcc       420
ccagtggtct gtgaattccc ggggtgatt tcactcccg gctgtccca ggcttgtccc         480 tgctacccc acccagcctt tcctgaggcc tcaagctgcc accagcccc cagctccttc         540 tccccgcaga cccaaacaca ggcctcagga ctcaacacag cttttccctc caacccgtt       600 ttctctccct caaggactca gctttctgaa gcccctccca gttctagttc tatcttttc      660 ctgcatcctg tctggaagtt agaaggaaac agaccacaga cctggtcccc aaagaaatg      720 gaggcaatag gttttgaggg gcatgggac ggggttcagc ctccagggtc ctacacacaa      780
atcagtcagt ggcccagaag acccccctcg gaatcggagc agggaggatg gggagtgtga    840
ggggtatcct tgatgcttgt gtgtcccccaa cttttccaaat nccgccccc gcgatggaga     900 agaaaccgag acagaaggtg cagggcccac taccgcttcc tccagatgag cttatgggtt     960
tctccaccaa ggaagttttc cgctggttga atgattcttt ccccgccctc ctctcgcccc   1020
agggacatat aaaggcagtt gttggcacac ccagccagca gacgctccct cagcaaggac    1080
agcagaggac cagctaagag ggagagaagc aactgcagac ccccctgaa acaaccctc       1140 agacgccaca tccctgaca agctgccagg caggttct                              1178
```

<210> SEQ ID NO 2
<211> LENGTH: 1096
<212> TYPE: DNA
<213> ORGANISM: Human
<220> FEATURE:
<223> OTHER INFORMATION: Human TNF-alpha promoter

<400> SEQUENCE: 2

```
gaggccgcca gactgctgca ggggaagcaa aggagaagct gagaagatga aggaaaagtc     60
agggtctgga ggggcggggg tcagggagct cctgggagat atggccacat gtagcggctc    120
tgaggaatgg gttacaggag acctctgggg agatgtgacc acagcaatgg gtaggagaat    180
gtccagggct atggaagtcg agtatgggga ccccccctta acgaagacag gccatgtag     240 agggccccag ggagtgaaag agcctccagg acctccaggt atggaataca ggggacgttt    300
aagaagatat ggccacacac tggggccctg agaagtgaga gcttcatgaa aaaaatcagg    360 accccagag ttccttggaa gccaagactg aaaccagcat tatgagtctc cgggtcagaa      420
tgaaagaaga aggcctgccc cagtggggtc tgtgaattcc cggggtgat ttcactcccc      480 ggggctgtcc caggcttgtc cctgctaccc ccacccagcc tttcctgagg cctcaagcct    540
gccaccaagc cccagctcc ttctccccgc agggacccaa acacaggcct caggactcaa     600
cacagctttt cctccaacc ccgttttctc tccctcaagg actcagcttt ctgaagcccc     660
tcccagttct agttctatct ttttcctgca tcctgtctgg aagttagaag gaaacagacc    720
acagacctgg tccccaaaag aaatggaggc aataggtttt gaggggcatg ggacggggt    780 tcagcctcca gggtcctaca cacaaatcag tcagtggccc agaagacccc ctcggaatc   840 ggagcaggga ggatggggag tgtgagggt atccttgatg cttgtgtgtc cccaactttc    900
caaatccccg ccccgcgat ggagaagaaa ccgagacaga aggtgcaggg cccactaccg    960
cttcctccag atgagctcat gggtttctcc accaaggaag ttttccgctg gttgaatgat  1020 tcttcccg ccctcctctc gccccaggga catataaagg cagttgttgg cacacccagc    1080
```
cagcagacgc tccctc                                                        1096

<210> SEQ ID NO 3
<211> LENGTH: 139
<212> TYPE: DNA
<213> ORGANISM: Human
<220> FEATURE:
<223> OTHER INFORMATION: native minimal TNF-alpha promoter

<400> SEQUENCE: 3
ccgcttcctc cagatgagct catgggtttc tccaccaagg aagttttccg ctggttgaat      60
gattctttcc ccgccctcct ctcgcccag ggacatataa aggcagttgt atggcacacc     120
cgccagcaga cgctccctc                                                    139

<210> SEQ ID NO 4
<211> LENGTH: 123
<212> TYPE: DNA
<213> ORGANISM: Human
<220> FEATURE:
<223> OTHER INFORMATION: TNF-alpha promoter enhancer region 1 (ER1)

<400> SEQUENCE: 4
ggggcggggg tcagggagct cctgggagat atggccacat gtagcggctc tgaggaatgg      60
gttacaggag acctctgggg agatgtgacc acagcaatgg gtaggagaat gtccagggct     120
atg                                                                     123

<210> SEQ ID NO 5
<211> LENGTH: 190
<212> TYPE: DNA
<213> ORGANISM: Human
<220> FEATURE:
<223> OTHER INFORMATION: TNF-alpha promoter enhancer region 2 (ER2)

<400> SEQUENCE: 5
tccttggaag ccaagactga aaccagcatt atgagtctcc gggtcagaat gaaagaagaa       60
ggcctgcccc agtgggtct gtgaattccc gggggtgatt tcactccccg gggctgtccc     120
aggcttgtcc ctgctacccc cacccagcct ttcctgaggc ctcaagcctg ccaccaagcc     180
cccagctcct                                                              190

<210> SEQ ID NO 6
<211> LENGTH: 223
<212> TYPE: DNA
<213> ORGANISM: Human
<220> FEATURE:
<223> OTHER INFORMATION: multiple cloning sites genetically engineered
      upstream of the minimal TNF-alpha promoter in the
      -120pGL3 construct

<400> SEQUENCE: 6
ggtaccgagc tcttacgcgt gctagccgcg gatatcttaa gacgtcctag gactagtcag       60
ctgctcgagc cgcttcctcc agatgagctc atgggtttct ccaccaagga agttttccgc     120
tggttgaatg attctttccc cgccctcctc tcgcccagg gacatataaa ggcagttgtt      180
ggcacaccca gccagcagac gctccctcag cagatctaag ctt                         223

<210> SEQ ID NO 7
<211> LENGTH: 787
<212> TYPE: DNA
<213> ORGANISM: Human
<220> FEATURE:

<223> OTHER INFORMATION: TNF-alpha untranslated region

<400> SEQUENCE: 7

| | | | | | |
|---|---|---|---|---|---|
| tctagaggag | gacgaacatc | caaccttccc | aaacgcctcc | cctgcccaa | tcccttat | 60 |
| accccctcct | tcagacaccc | tcaacctctt | ctggctcaaa | aagagaattg | ggggcttagg | 120 |
| gtcggaaccc | aagcttagaa | ctttaagcaa | caagaccacc | acttcgaaac | ctgggattca | 180 |
| ggaatgtgtg | gcctgcacag | tgaagtgctg | gcaaccacta | agaattcaaa | ctggggcctc | 240 |
| cagaactcac | tggggcctac | agctttgatc | cctgacatct | ggaatctgga | gaccagggag | 300 |
| cctttggttc | tggccagaat | gctgcaggac | ttgagaagac | ctcacctaga | aattgacaca | 360 |
| agtggacctt | aggccttcct | ctctccagat | gtttccagac | ttccttgaga | cacggagccc | 420 |
| agccctcccc | atggagccag | ctccctctat | ttatgtttgc | acttgtgatt | atttattatt | 480 |
| tatttattat | ttatttattt | acagatgaat | gtatttattt | gggagaccgg | ggtatcctgg | 540 |
| gggacccaat | gtaggagctg | ccttggctca | gacatgtttt | ccgtgaaaac | ggagctgaac | 600 |
| aataggctgt | tcccatgtag | ccccctggcc | tctgtgcctt | cttttgatta | tgttttttaa | 660 |
| aatatttatc | tgattaagtt | gtctaaacaa | tgctgatttg | gtgaccaact | gtcactcatt | 720 |
| gctgagcctc | tgctccccag | gggagttgtg | tctgtaatcg | ccctactatt | cagtggcgag | 780 |
| atctaga | | | | | | 787 |

<210> SEQ ID NO 8
<211> LENGTH: 839
<212> TYPE: DNA
<213> ORGANISM: Human
<220> FEATURE:
<223> OTHER INFORMATION: full length Granzyme B

<400> SEQUENCE: 8

| | | | | | |
|---|---|---|---|---|---|
| atgcaaccaa | tcctgcttct | gctggccttc | ctcctgctgc | ccagggcaga | tgcaggggag | 60 |
| atcatcgggg | gacatgaggc | caagccccac | tcccgcccct | acatggctta | tcttatgatc | 120 |
| tgggatcaga | agtctctgaa | gaggtgcggt | ggcttcctga | taagacga | cttcgtgctg | 180 |
| acagctgctc | actgttgggg | aagctccata | aatgtcacct | gggggccca | caatatcaag | 240 |
| gaacaggagc | cgacccagca | gtttatccct | gtgaaaagag | ccatccccca | tccagcctat | 300 |
| aatcctaaga | acttctccaa | tgacatcatg | ctactgcagc | tggagagaaa | ggccaagcgg | 360 |
| accagagctg | tgcagccct | caggctacct | agcaacaagg | cccaggtgaa | gccagggcag | 420 |
| acatgcagtg | tggccggctg | ggggcagacg | gccccctgg | aaaacactc | acacacacta | 480 |
| caagaggtga | agatgacagt | gcaggaagat | cgaaagtgcg | aatctgactt | acgccattat | 540 |
| tacgacagta | ccattgagtt | gtgcgtgggg | gacccagaga | ttaaaaagac | ttcctttaag | 600 |
| ggggactctg | gaggccctct | tgtgtgtaac | aaggtggccc | agggcattgt | ctcctatgga | 660 |
| cgaaacaatg | gcatgcctcc | acgagcctgc | accaaagtct | caagctttgt | acactggata | 720 |
| aagaaaacca | tgaaacgcta | ctaactacag | gaagcaaact | aagcccccgc | tgtaatgaaa | 780 |
| caccttctct | ggagccaagt | ccagatttac | actgggagag | gtgccagcaa | ctgaataaa | 839 |

<210> SEQ ID NO 9
<211> LENGTH: 782
<212> TYPE: DNA
<213> ORGANISM: Human
<220> FEATURE:
<223> OTHER INFORMATION: truncated Granzyme B (devoid of the leader
    peptide and inactivating di-peptide)

```
<400> SEQUENCE: 9
atgatcatcg ggggacatga ggccaagccc cactcccgcc cctacatggc ttatcttatg      60
atctgggatc agaagtctct gaagaggtgc ggtggcttcc tgatacaaga cgacttcgtg     120
ctgacagctg ctcactgttg gggaagctcc ataaatgtca ccttgggggc ccacaatatc     180
aaggaacagg agccgaccca gcagtttatc cctgtgaaaa gagccatccc catccagcc      240
tataatccta agaacttctc caatgacatc atgctactgc agctggagag aaaggccaag     300
cggaccagag ctgtgcagcc cctcaggcta cctagcaaca aggcccaggt gaagccaggg     360
cagacatgca gtgtggccgg ctgggggcag acggcccccc tgggaaaaca ctcacacaca     420
ctacaagagg tgaagatgac agtgcaggaa gatcgaaagt gcgaatctga cttacgccat     480
tattacgaca gtaccattga gttgtgcgtg ggggacccag agattaaaaa gacttccttt     540
aagggggact ctggaggccc tcttgtgtgt aacaaggtgg cccagggcat tgtctcctat     600
ggacgaaaca atggcatgcc tccacgagcc tgcaccaaag tctcaagctt tgtacactgg     660
ataaagaaaa ccatgaaacg ctactaacta caggaagcaa actaagcccc cgctgtaatg     720
aaacaccttc tctggagcca agtccagatt tacactggga gaggtgccag caactgaata     780
aa                                                                    782

<210> SEQ ID NO 10
<211> LENGTH: 833
<212> TYPE: DNA
<213> ORGANISM: Human
<220> FEATURE:
<223> OTHER INFORMATION: inactivating di-peptide deleted Granzyme B

<400> SEQUENCE: 10
atgcaaccaa tcctgcttct gctggccttc ctcctgctgc ccagggcaga tgcaatcatc      60
ggggacatg aggccaagcc ccactcccgc cctacatgg cttatcttat gatctgggat      120
cagaagtctc tgaagaggtg cggtggcttc ctgatacaag acgacttcgt gctgacagct     180
gctcactgtt ggggaagctc cataaatgtc accttggggg ccacaatat caaggaacag     240
gagccgaccc agcagtttat ccctgtgaaa agagccatcc ccatccagc ctataatcct     300
aagaacttct ccaatgacat catgctactg cagctggaga gaaaggccaa gcggaccaga     360
gctgtgcagc ccctcaggct acctagcaac aaggcccagg tgaagccagg gcagacatgc     420
agtgtggccg gctgggggca gacggccccc ctgggaaaac actcacacac actacaagag     480
gtgaagatga cagtgcagga agatcgaaag tgcgaatctg acttacgcca ttattacgac     540
agtaccattg agttgtgcgt ggggacccca gagattaaaa agacttcctt taaggggac     600
tctggaggcc ctcttgtgtg taacaaggtg gcccaggca ttgtctccta tggacgaaac     660
aatggcatgc ctccacgagc ctgcaccaaa gtctcaagct ttgtacactg gataaagaaa     720
accatgaaac gctactaact acaggaagca aactaagccc cgctgtaat gaaacacctt     780
ctctggagcc aagtccagat ttacactggg agaggtgcca gcaactgaat aaa            833

<210> SEQ ID NO 11
<211> LENGTH: 114
<212> TYPE: DNA
<213> ORGANISM: Human
<220> FEATURE:
<223> OTHER INFORMATION: enhancer region 3: -234 to -120 TNF-alpha
      promoter

<400> SEQUENCE: 11
```

-continued

| gcagggagga tgggagtgt gagggtatc cttgatgctt gtgtgtcccc aactttccaa | 60 |
| atccccgccc ccgcgatgga aagaaaccg agacagaagg tgcagggccc acta | 114 |

<210> SEQ ID NO 12
<211> LENGTH: 169
<212> TYPE: DNA
<213> ORGANISM: Human
<220> FEATURE:
<223> OTHER INFORMATION: enhancer region 4: -234 to -65 TNF-alpha
      promoter

<400> SEQUENCE: 12

| gcagggagga tggggagtgt gagggtatc cttgatgctt gtgtgtcccc aactttccaa | 60 |
| atccccgccc ccgcgatgga aagaaaccg agacagaagg tgcagggccc actaccgctt | 120 |
| cctccagatg agctcatggg tttctccacc aaggaagttt ccgctggt | 169 |

<210> SEQ ID NO 13
<211> LENGTH: 2270
<212> TYPE: DNA
<213> ORGANISM: Human
<220> FEATURE:
<223> OTHER INFORMATION: chimeric gene : -706TNFpGB3'UTR

<400> SEQUENCE: 13

| ctcgagtcct tggaagccaa gactgaaacc agcattatga gtctccgggt cagaatgaaa | 60 |
| gaagaaggcc tgccccagtg gggtctgtga attcccgggg gtgatttcac tccccggggc | 120 |
| tgtcccaggc ttgtccctgc tacccccacc cagccttttcc tgaggctcaa gcctgccacc | 180 |
| aagcccccag ctccttctcc ccgcaggac ccaaacacag gcctcaggac tcaacacagc | 240 |
| ttttccctcc aaccccgttt tctctccctc aaggactcag ctttctgaag cccctcccag | 300 |
| ttctagttct atcttttttcc tgcatcctgt ctggaagtta aaggaaaca gaccacagac | 360 |
| ctggtcccca aagaaatgg aggcaatagg ttttgagggg catgggacg gggttcagcc | 420 |
| tccagggtcc tacacacaaa tcagtcagtg gcccagaaga cccccctcgg aatcggagca | 480 |
| gggaggatgg ggagtgtgag gggtatcctt gatgcttgtg tgtccccaac tttccaaatc | 540 |
| cccgcccccg cgatggagaa gaaaccgaga cagaaggtgc agggcccact accgcttcct | 600 |
| ccagatgagc tcatgggttt ctccaccaag gaagttttcc gctggttgaa tgattctttc | 660 |
| cccgccctcc tctcgcccca gggacatata aaggcagttg ttggcacacc cagccagcag | 720 |
| acgctccctc agcagatcta tgcaaccaat cctgcttctg ctggccttcc tcctgctgcc | 780 |
| cagggcagat gcaatcatcg ggggacatga ggccaagccc cactcccgcc ctacatggc | 840 |
| ttatcttatg atctgggatc agaagtctct gaagaggtgc ggtggcttcc tgatacaaga | 900 |
| cgacttcgtg ctgacagctg ctcactgttg gggaagctcc ataaatgtca ccttgggggc | 960 |
| ccacaatatc aaagaacagg agccgaccca gcagtttatc cctgtgaaaa gacccatccc | 1020 |
| ccatccagcc tataatccta agaacttctc caacgacatc atgctactgc agctggagag | 1080 |
| aaaggccaag cggaccagag ctgtgcagcc cctcaggcta cctagcaaca aggcccaggt | 1140 |
| gaagccaggg cagacatgca gtgtggccgg ctgggggcag acggccccc tgggaaaaca | 1200 |
| ctcacacaca ctacaagagg tgaagatgac agtgcaggaa gatcgaaagt gcgaatctga | 1260 |
| cttacgccat tattacgaca gtaccattga gttgtgcgtg ggggacccag agattaaaaa | 1320 |
| gacttccttt aagggggact ctggaggccc tcttgtgtgt aacaaggtgg cccagggcat | 1380 |
| tgtctcctat ggacgaaaca atggcatgcc tccacgagcc tgcaccaaag tctcaagctt | 1440 |

-continued

```
tgtacactgg ataaagaaaa ccatgaaacg ctactaagaa ttctctagag gaggacgaac    1500
atccaacctt cccaaacgcc tccctgccc caatccctt attacccct ccttcagaca       1560
ccctcaacct cttctggctc aaaaagagaa ttgggggctt agggtcggaa cccaagctta    1620
gaactttaag caacaagacc accacttcga aacctgggat tcaggaatgt gtggcctgca    1680
cagtgaagtg ctggcaacca ctaagaattc aaactgggc ctccagaact cactggggcc     1740
tacagctttg atccctgaca tctggaatct ggagaccagg gagcctttgg ttctggccag    1800
aatgctgcag gacttgagaa gacctcacct agaaattgac acaagtggac cttaggcctt    1860
cctctctcca gatgtttcca gacttccttg agacacggag cccagccctc ccatggagc     1920
cagctccctc tatttatgtt tgcacttgtg attatttatt atttatttat tatttattta    1980
tttacagatg aatgtattta tttgggagac cggggtatcc tgggggaccc aatgtaggag    2040
ctgccttggc tcagacatgt tttccgtgaa acggagctg aacataggc tgttcccatg      2100
tagccccctg gcctctgtgc cttcttttga ttatgttttt taaaatattt atctgattaa    2160
gttgtctaaa caatgctgat ttggtgacca actgtcactc attgctgagc ctctgctccc    2220
cagggagtt gtgtctgtaa tcgccctact attcagtggc gagatctaga                2270
```

<210> SEQ ID NO 14
<211> LENGTH: 2570
<212> TYPE: DNA
<213> ORGANISM: Human
<220> FEATURE:
<223> OTHER INFORMATION: chimeric gene : -1005TNFpGB3'UTR

<400> SEQUENCE: 14

```
ctcgagggcg ggggtcaggg agctcctggg agatatggcc acatgtagcg gctctgagga     60
atgggttaca ggagacctct ggggagatgt gaccacagca atgggtagga aatgtccag     120
ggctatggaa gtcgagtatg ggacccccc cttaacgaag acagggccat gtagagggcc     180
ccagggagtg aaagagcctc caggacctcc aggtatggaa tacagggac gtttaagaag    240
atatggccac acactgggc cctgagaagt gagagcttca tgaaaaaaat cagggacccc    300
agagttcctt ggaagccaag actgaaacca gcattatgag tctccgggtc agaatgaaag   360
aagaaggcct gccccagtgg ggtctgtgaa ttccgggggg tgattcact ccccggggct    420
gtcccaggct tgtccctgct accccaccc agcctttcct gaggcctcaa gcctgccacc    480
aagccccag ctccttctcc ccgcaggac ccaaacacag gcctcaggac tcaacacagc     540
tttttccctcc aaccccgttt tctctccctc aaggactcag cttctgaag cccctcccag   600
ttctagttct atcttttcc tgcatcctgt ctggaagtta aaggaaaca gaccacagac     660
ctggtcccca aaagaaatgg aggcaatagg ttttgagggg catgggacg gggttcagcc    720
tccagggtcc tacacacaaa tcagtcagtg gcccagaaga ccccctcgg aatcggagca   780
gggaggatgg ggagtgtgag gggtatcctt gatgcttgtg tgtccccaac tttccaaatc    840
cccgccccg cgatggagaa gaaccgaga cagaaggtgc agggcccact accgcttcct    900
ccagatgagc tcatgggttt ctccaccaag gaagttttcc gctggttgaa tgattctttc    960
cccgccctcc tctcgcccca gggacatata aaggcagttg ttggcacacc cagccagcag   1020
acgctccctc agcagatcta tgcaaccaat cctgcttctg ctggccttcc tcctgctgcc    1080
cagggcagat gcaatcatcg gggacatga ggccaagccc cactcccgcc ctacatggc    1140
ttatcttatg atctgggatc agaagtctct gaagaggtgc ggtggcttcc tgatacaaga    1200
cgacttcgtg ctgacagctg ctcactgttg gggaagctcc ataaatgtca ccttgggggc   1260
```

```
ccacaatatc aaagaacagg agccgaccca gcagtttatc cctgtgaaaa gacccatccc      1320
ccatccagcc tataatccta agaacttctc caacgacatc atgctactgc agctggagag      1380
aaaggccaag cggaccagag ctgtgcagcc cctcaggcta cctagcaaca aggcccaggt      1440
gaagccaggg cagacatgca gtgtggccgg ctgggggcag acggcccccc tgggaaaaca      1500
ctcacacaca ctacaagagg tgaagatgac agtgcaggaa gatcgaaagt gcgaatctga      1560
cttacgccat tattacgaca gtaccattga gttgtgcgtg ggggacccag agattaaaaa      1620
gacttccttt aagggggact ctggaggccc tcttgtgtgt aacaaggtgg cccagggcat      1680
tgtctcctat ggacgaaaca atggcatgcc tccacgagcc tgcaccaaag tctcaagctt      1740
tgtacactgg ataaagaaaa ccatgaaacg ctactaagaa ttctctagag gaggacgaac      1800
atccaacctt cccaaacgcc tcccctgccc caatccctt attaccccct ccttcagaca      1860
ccctcaacct cttctggctc aaaaagagaa ttgggggctt agggtcggaa cccaagctta      1920
gaactttaag caacaagacc accacttcga aacctgggat tcaggaatgt gtggcctgca      1980
cagtgaagtg ctggcaacca ctaagaattc aaactgggc ctccagaact cactgggcc        2040 tacagctttg atccctgaca tctggaatct ggagaccagg gagcctttgg ttctggccag      2100
aatgctgcag gacttgagaa gacctcacct agaaattgac acaagtggac cttaggcctt      2160
cctctctcca gatgtttcca gacttccttg agacacggag cccagccctc cccatggagc      2220
cagctccctc tatttatgtt tgcacttgtg attatttatt atttatttat tatttattta      2280
tttacagatg aatgtattta tttgggagac cggggtatcc tgggggaccc aatgtaggag      2340
ctgccttggc tcagacatgt tttccgtgaa aacggagctg aacaataggc tgttcccatg      2400
tagccccctg gcctctgtgc cttcttttga ttatgttttt taaaatattt atctgattaa      2460
gttgtctaaa caatgctgat ttggtgacca actgtcactc attgctgagc ctctgctccc      2520
caggggagtt gtgtctgtaa tcgccctact attcagtggc gagatctaga              2570
```

<210> SEQ ID NO 15
<211> LENGTH: 10
<212> TYPE: DNA
<213> ORGANISM: Human
<220> FEATURE:
<223> OTHER INFORMATION: KappaB3 sequence

<400> SEQUENCE: 15

```
gggtttctcc                                                              10
```

SELF-REGULATED APOPTOSIS OF INFLAMMATORY CELLS BY GENE THERAPY

RELATED APPLICATION

The benefit of co-pending provisional application Ser. No. 60/076,316, filed on Feb. 27, 1998.

TECHNICAL FIELD OF THE INVENTION

The present invention relates to the fields of molecular biology and immunology. More specifically, this invention relates to the induction of apoptosis in inflammatory cells by introducing into those cells a gene which induces apoptosis (programmed cell death or non-necrotic cell death) in these cells.

BACKGROUND OF THE INVENTION

In many inflammatory conditions, cytokines such as IL-1β, IL-10, GM-CSF and TNFα are excessively produced as a result of mass aggregation and accumulation of inflammatory cells (Brennan F. M. et al., *British Medical Bulletin* 1995, 51/2, 368–384). Upregulation and/or dysregulation of cytokines in inflamed tissue may be directly or indirectly responsible for exacerbation of chronic inflammatory diseases. For example, the most marked pathology in rheumatoid arthritis (RA) is displayed at the local site of inflammation (i.e., the synovial joints). Therefore, it is likely that the cytokines produced in the synovial joints of RA patients play an important role in the disease process. Of those cytokines, IL-1β and TNFα are believed to be responsible for the devastating cartilage destruction and bone erosion which characterizes RA (Dayer J. M. et al., *J. Exp. Med.*, 1985, 162, 1208–1215; Gowen M. et al., *Nature*, 1983, 306, 378–380). The presence of excessive amounts of IL-1β and TNFα in the synovial joints has been shown to accelerate development of collagen-induced arthritis in rodents (Brennan F. M., et al., *Clin. Expt. Immunol.*, 1994, 97/1, 1–3).

Apoptosis is a fundamental physiological process for embryonic development and maintenance of tissue homeostasis. (Raff, M. C. Nature, 1992, 356, 397; Vaux, D. L. et al. Cell, 1994, 76, 777). Inconsistency in this critical natural process is featured in a variety of neoplastic, neurodegenerative and autoimmune diseases (Thompson, C. B., Science, 1995, 267, 1456). Biochemical attributes, involving signal transduction cascade, are relatively complex and are not completely understood. A variety of stimuli including activation of specific receptors, such as TNFR1 or Fas trigger evolutionary conserved execution machinery involving several signaling components, that are orchestrated to cause cellular demise (Ashkenazi, A. and Dixit, V. M., Science, 1998, 181, 1305).

Granzyme B is a serine protease, primarily found in cytoplasmic granules of cytotoxic T lymphocytes and natural killer cells. Granzyme B plays an important role in inducing apoptotic changes in target cells by cytotoxic cell mediated killing (Huesel J. W. et al, Cell, 76, 977–987, 1994; Shi, L. et al. J. Exp. Med. 176,1521–1529, 1992), partly by catalyzing cleavage and activation of several caspases (Salvesen, G. S. and Dixit, V. M., Cell, 91, 443–446, 1997) as well as by caspase independent pathways (Andrade, F. et al. Immunity 8,451–460,1998). Structurally, Granzyme B is produced as polypeptide containing a leader peptide separated by an inactivating di-peptide (Gly-Glu) from the active Granzyme B polypeptide. Like the caspases, Granzyme B recognizes substrates specifically at aspartic acid for cleavage.

TNFα is a cytokine, mainly synthesized by monocytes, macrophages and lymphocytes in response to activation. The classic elements governing its expression are located in the proximal or the distal promoter region (reviewed in Pauli, U. Critical Rev. in Eukaryotic Gene Expression, 1994, 4, 323–344). Summarized below are regions that have been described to play a significant role in the TNFα promoter activity:

a) TNFα-responsive elements were shown to be located between base pairs −100 to −125. The region −108 to −101bp contains a palindrome, TGAGCTCA, which is similar to AP-1 sequence that contains PMA-responsive elements. Multiple copies of −125 to −85bp confer a 7 to 11 fold induction of the expression of the reporter gene (Leitman, D. et al, J. Biol. Chem. 266, 9343, 1991).

b) PMA-responsive elements were shown to be present in between −101 to −286 base pairs (Hensel, G. et al, Lymphokine Res. 8, 347, 1989).

c) Anti-CD3 antibody-induced (as well as Ca-ionophore-induced) responsive elements were shown to lie between −118 to −80 base pairs. The KappaB3 (GGGTTTCTCC) SEQ ID NO: 15 sequence in this region is of high importance for CsA-sensitive activation of the TNFα promoter by Ca-ionophore. These elements are suggested to be optimally functional in the context of their own promoter (Goldfield, et al. J. Exp. Med. 178, 1356, 1993).

d) In U937 cells, the PMA responsive element is located between −95 to −36bp and the cAMP-responsive element (CRE) is mapped to position −107 to-99bp. This region does not respond to PMA (Economou, J. S. et al , J. Exp. Med. 170, 321, 1989).

e) All three kappaB sites [viz. kappaB1 (−587 to −577), kappaB2 (−210 to −202) and kappaB3 (−98 to −87)]bound virus-inducible protein, although deletion of these sites did not affect virus inducibility (Goldfield, A. et al, PNAS, 87, 9769, 1990). Further more, deletion mutants of kappaB sites show that they are not primary targets for PMA stimulation of human TNFα gene (Goldfield, A. et al J. Exp. Med. 174, 73, 1991).

f) In the murine system, the TNFα promoter constructs −1059, −695 and −655bp are strongly LPS inducible. This LPS-inducibility was greatly reduced in a −451bp construct and further between −301 and −241bp. The −1059bp fragment of TNFα promoter was silent in macrophages and was strongly expressed after LPS stimulation. The largest drop of activation was at −695 to −655bp, which contains a kappaB element in the murine TNFα promoter (Shakhov, A. N. et al, J. Exp. Med., 1990, 171,35; Drouet, C. et al, J. Immunol., 1991, 147, 1694).

Elements in the 3' untranslated region (3'UTR) of the TNFα gene are known to be important for post-transcriptional regulation. Analysis of the influence of 3' UTR has been made in the murine system, wherein conjunction with the homologous promoter, LPS inducibility was very strong. Using murine TNFα promoter system, it was shown that 3'UTR effectively inhibits CAT activity in three non-macrophage cell lines viz. HeLa, NIH3T3 and L929. The sequence TTATTTAT was repeated several times in the 3'UTR and was proposed to be involved in regulation (Han, J., et al., *J. Immunology*, 1991, 146, 1843–1848; Crawford, F. K., et al., *J. Biol. Chem.*, 1996, 271, 22383–22390).

A variety of cells such as activated macrophages, activated T cells, macrophage-like synoviocytes as well as fibroblasts-like synoviocytes, and transformed macrophage-like synoviocytes (also referred to as pannocyte) are present in the inflamed joints. An invasive structure, called the pannus, derives from the hyperplastic nature of synoviocytes and pannocytes. The pannus may result from an excessive proliferation of cells and/or diminished apoptosis in these cells. Proliferative index in these cells was shown to be relatively low. Therefore, hyperplasia in synoviocytes could be due to abnormalities in apoptosis of the synovial lining. The frequency of cells with end stage apoptosis is low in the synovium. Abnormalities of p53 mutations, which could result in resistance to apoptosis are reported in the RA synovial fibroblasts. Additionally, excessive amounts of pro-inflammatory cytokines such as TNFα and IL-1β are produced in the synovial tissue by a variety of cell types at the cartilage-pannus junction, including cells of the macrophage lineage, macrophage-like synoviocytes, activated T-cells and possibly fibroblast-like synoviocytes (Chu C. Q. et al., *Arthritis & Rheumatism*, 1991, 34, 1125–1132; Deleuran B. W., et al., *Arthritis & Rheumatism*, 1992, 35, 1170–1178). This perpetuates the infiltration of inflammatory cells and production of more pro-inflammatory cytokines and factors, which are responsible for synovial cell proliferation. In addition to the above described inflammatory effects, TNFα plays a ubiquitous and key role in a variety of pro-inflammatory events.

TNFα induces IL-1β activity in monocytes. Indeed, anti-TNFα neutralizing antibodies have been shown to reduce overall IL-1β production (Portillo, et al., *Immunol.*, 1989, 66, 170–175; Brennan F. M., et al., *British Medical Bulletin* 1995, 51/2, 368–384). Thus, an added benefit to blocking the effect of the inflammatory cytokine TNFα was the reduction in production of the equally destructive pro-inflammatory mediator, IL-β. Furthermore, it is well known that TNFα is a transcriptional activator of other inflammation-related genes. For example, the presence of TNFα stimulates production of other cytokines (such as GM-CSF) and cell surface receptors, including HLA class II antigens and adhesion molecules (Alvaro-Garcia J. M., et al., *J. Exp. Med.*, 1989, 146, 865–875), that perpetuate recruitment of activated T cells and neutrophils resulting in synovial inflammation and hyperplasia and ultimately, in augmented destruction of cartilage and bone (Allen J. B., *J. Exp. Med.*, 1990, 171, 231).

Conventional therapy against inflammatory disorders is typically directed against symptomatic inflammation. Such therapy provides only temporary relief without significantly delaying disease progression. In contrast, therapies targeting TNFα and other factors induced in the inflammatory process are likely to be more promising. For example, in collagen-induced arthritis animal models, an anti-TNFα antibody and soluble TNFα receptor-IgG chimera effectively reduced paw swelling, joint involvement and cartilage and bone destruction (Williams R. O. et al., *Proc. Natl. Acad. Sci.*, 1992, 89, 9784–9788). Human trials using both humanized anti-TNFα antibodies and TNFα receptor-IgG chimeric molecules produced dramatic results (Elliott M. J., et al., *Arthritis and Rheumatism*, 1993, 36, 1681–1690; Elliott M. J., et al., *Lancet*, 343, 1105–1110). Although treatment with these TNFα antagonists appears to be well tolerated, it also results in production of antibodies against the recombinant proteins. Thus, these therapies may not be suitable for long term treatment and do not achieve true disease abatement.

WO 97/07828 discloses methods of treating by gene therapy a patient with cellular accumulation or a chronic inflammatory disease which was a result of a defective apoptosis-regulating gene, more specifically p53. The treatment restores the defect with a wild-type gene attached to a promoter which drives the apoptosis-regulating gene expression.

In order to actually modify progression of the disease, TNFα must be continuously targeted using TNFα-specific therapies. Such a continuous therapeutic protocol was impractical with these biologic agents and would be difficult to administer in the long term.

In an alternate therapeutic option, inflamed synovium may be removed using surgical (Herold N. and Schroder H. A., *Acta Orthop. Scand.*, 1995, 66, 252–254; Ogilvie-Harris D. J. and Weisleder L., *Arthroscopy*, 1995, 11, 91–95), chemical (Cruz-Esteban C. and Wilke W. S., *Bailliere's Clinical Rheumatol.*, 1995, 9, 787–801) or radiation-induced synovectomy (Cruz-Esteban C. and Wilke W. S., *Bailliere's Clinical Rheumatol.*, 1995, 9, 787–801). Marginal to good results follow arthroscopic surgery. Non-surgical synovectomy is performed using various chemical agents such as osmic acid, alkylating agents such as nitrogen mustard and thiotepa, methotrexate. Unfortunately, non-surgical synovectomies (including chemical and radiation-induced) are procedurally complicated, provide only short term relief and show only patchy reduction of the synovial hyperplasia. Furthermore, most of the non-surgical alternatives are potential teratogens. Moreover, an innate inflammatory response is concomitant with tissue damage arising from the chemical or surgical intervention. Finally, it should be noted that these approaches suffer from the risks and side-effects commonly associated with conventional pharmaceutical therapy and invasive surgical procedures, including the expense and inconvenience of hospitalization and rehabilitation.

Accordingly, a need still exists for an effective therapeutic approach to treating inflammatory disorders in general and RA in particular.

SUMMARY OF THE INVENTION

The invention provides methods and compositions relating to a novel apoptosis induced destruction of TNFα producing cells. It was therefore an object of the invention to provide unique chimeric nucleic acid molecules having at least one TNFα promoter enhancer region (comprising the nucleic acid SEQ ID NO: 4, SEQ ID NO: 5, SEQ ID NO: 11, SEQ ID NO: 12 or conservative substitution or allelic variants thereof) attached to a TNFα promoter, the TNFα promoter further being attached to a nucleic acid sequence encoding the Granzyme B protein or conservative substitution or allelic variants thereof which in turn was further attached to a 3'UTR nucleic acid sequence.

Another objective of this invention was to provide TNFp-AIG and the like chimeric nucleic acid constructs, processes for making them, methods of using them, and preparations containing them.

It was a further object to provide a method of treating an inflammatory disorder by administering to a patient in need of such treatment a pharmaceutically effective amount of the composition having the chimeric nucleic acid molecule described herein.

It was yet a further objective of this invention to provide a method for the induction of apoptosis in cells transfected with the TNFp-AIG chimeric nucleic acid, a method for the in vitro selection of TNFα non-producer somatic cell variants in a population, a method for identifying dominant/negative genes responsible for the genesis of a TNFα non-producing population and a method for identifying products responsible for regulation of TNFα production.

These and other objectives will be readily appreciated by those of ordinary skill in the art based upon the following detailed disclosure of the invention.

BRIEF DESCRIPTION OF THE FIGURES

FIG. 12 is a graphical representation of the chimeric nucleic acid −706TNFpGB3'UTR (SEQ ID NO: 13) sequence wherein the promoter fragment sequence is denoted by lower case alphabet, the linker fragment sequence is denoted by upper case italicized alphabet, the Granzyme B fragment sequence is denoted by upper case alphabet, and the TNFα3'UTR fragment sequence is denoted by lowercase underlined alphabet.

FIG. 13 is a graphical representation of the chimeric nucleic acid −1005TNFpGB3'UTR (SEQ ID NO: 14) sequence wherein the promoter fragment sequence is denoted by lower case alphabet, the linker fragment sequence is denoted by upper case italicized alphabet, the Granzyme B fragment sequence is denoted by upper case alphabet, and the TNFα3'UTR fragment sequence is denoted by lowercase underlined alphabet.

DETAILED DESCRIPTION OF THE INVENTION

Figure 1:
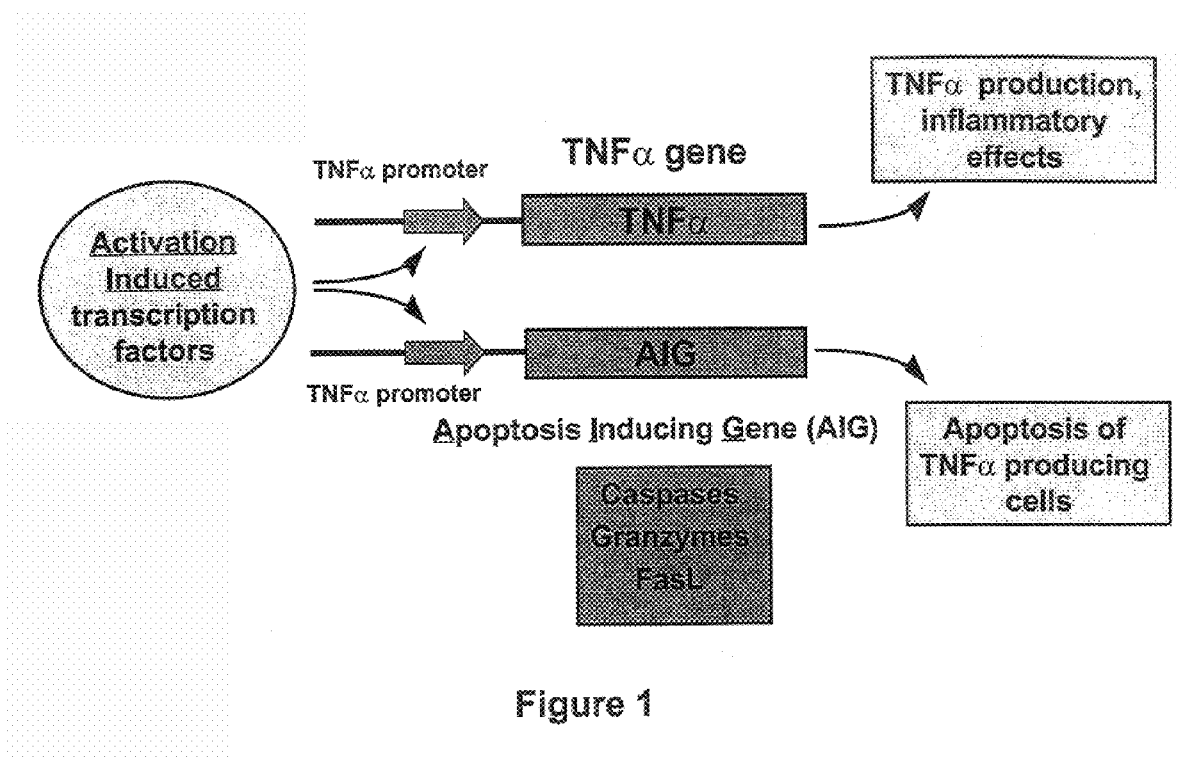
FIG. 1 is a schematic representation of TNFp-AIG chimeric nucleic acids of this invention. The Apoptosis Inducing Gene (AIG) is Granzyme B.
Figure 2:
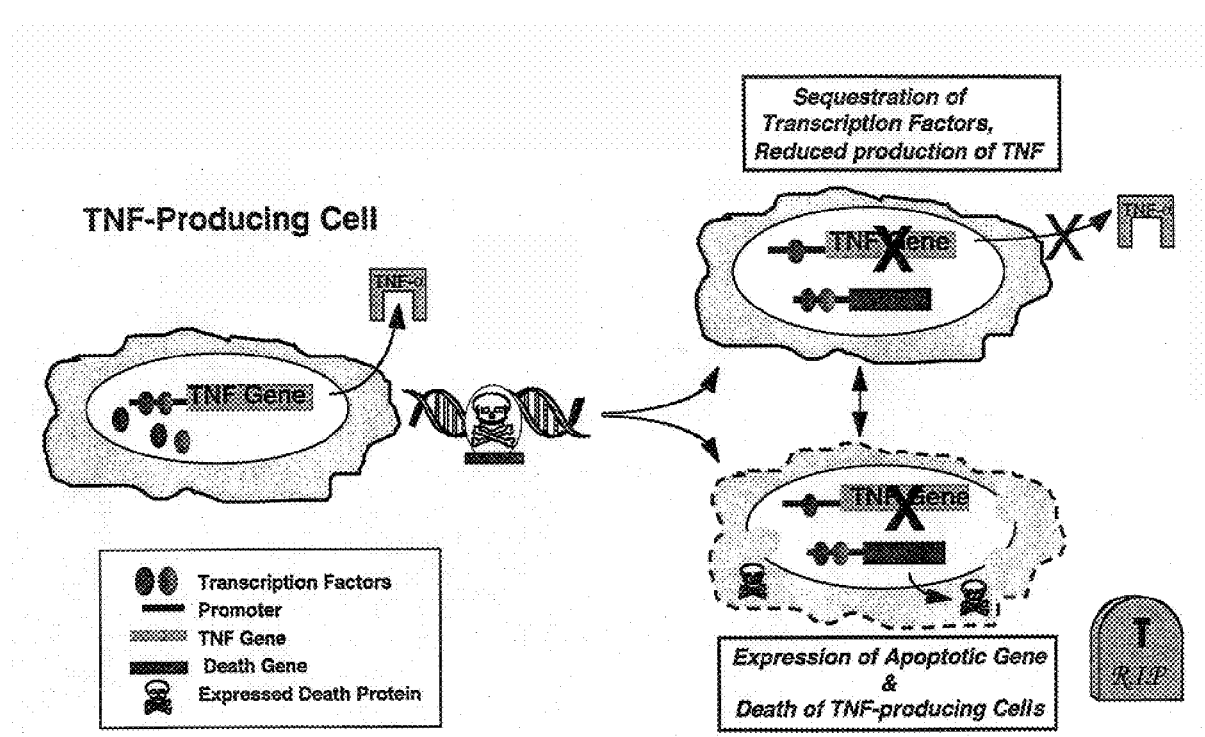
FIG. 2 is a schematic drawing depicting the results of gene therapy using a TNFp-AIG chimeric nucleic acids of this invention.

The invention described herein overcomes the drawbacks in the field by providing novel chimeric nucleic acid molecules for use in therapeutic compositions and methods of using such compositions. The compositions are directed to selectively induce apoptosis in TNFα producing cells causing destruction of these cells.

As used herein, the abbreviation 3'UTR means 3' untranslated region.

The abbreviation "AIG" refers to Apoptosis Inducing Gene. An AIG includes Granzyme B.

The abbreviation "CsA" refers to Cyclosporin A, a biologically active fungal metabolite with immunosuppressive properties.

The abbreviation "DN" refers to dominant/negative gene products which have negative affect on expression or function of other genes or gene products.

The abbreviation "ER" refers to Enhancer Region, whereby ER1 has SEQ ID NO: 4, ER2 has SEQ ID NO: 5, ER3 has SEQ ID NO: 11, and ER4 has SEQ ID NO: 12.

The abbreviation "GB" refers to Granzyme B.

The abbreviation "PMA" refers to Phorbol Myristate Acetate.

The abbreviation "RA" refers to Rheumatoid Arthritis.

The abbreviation "TNFα" refers to tumor necrosis factor alpha.

The terms "TNF promoter", "TNFα promoter" and "TNFp" are used interchangeably herein. Unless noted to the contrary, these terms refer to the entire nucleotide sequence corresponding to a native TNFα minimal promoter sequence attached to one or more upstream enhancer elements, either present naturally, native, or genetically engineered in the laboratory.

Amino acid "substitutions" are defined as having one for one amino acid replacements. They are conservative in nature when the substituted amino acid has similar structural and/or chemical properties. Examples of conservative replacements are substitution of a leucine with an isoleucine or valine, an aspartate with a glutamate, or a theronine with a serine.

"Conservative variants" refer to the substitutions of amino acids in a polypeptide.

"Allelic variants" refer to the variation at the nucleic acid and protein level either due to conservative or non-conservative substitutions giving rise to alternative form of the same gene.

"Reporter" molecules are chemical moieties used for labelling a nucleic acid or amino acid sequence. They include, but are not limited to, radionuclides, enzymes, fluorescent, chemiluminescent, or chromogenic agents. Reporter molecules associate with, establish the presence of, and may allow quantification of a particular nucleic or amino acid sequence.

"Reporter genes" are nucleic acids and fragments thereof encoding a functional protein, such as luciferase, that may be used to assess the activity of heterologous promoters.

A "functional fragment" of a polynucleotide or nucleic acid comprises all or any part of the nucleotide sequence having fewer nucleotides, which can be used as genetic material sufficient to initiate transcription of a gene or encode for a functional subunit of a polypeptide.

This invention was based upon evidence that apoptosis of inflammatory cells in certain inflammatory diseases was therapeutically beneficial. The invention specifically relates to self-regulated apoptosis by gene therapy. Broadly speaking, in the practice of the invention, a chimeric nucleic acid comprising at least one promoter enhancer attached to at least one functional copy of a minimal promoter, the promoter being a gene or combination of genes activated in inflammatory cells or in cells at a site of inflammation, was attached to at least one copy of an apoptosis-inducing gene (AIG), such that the expression of the AIG was driven by the promoter, thus targeting the inflammatory cells. The promoters of inducible genes activated in inflammation include the nucleic acid sequence of the TNFα promoter and conservative substitution or allelic variants thereof. Chimeric nucleic acids according to the invention comprise enhancer, promoter, and AIG elements in direct, distal, or proximal attachment, and combinations thereof. As mentioned above and will be discussed in more detail below, in some embodiments, multiple copies of the enhancer, promoter, and/or AIG were employed for maximal efficacy.

In order that the invention herein described may be more fully understood, the following detailed description is set forth, with emphasis on chimeric nucleic acids comprising at least one TNFα promoter enhancer attached to at least one functional copy of a minimal TNFα promoter and further attached to at least one copy of an AIG for illustrative purposes only. Though the examples that follow also employ these types of constructions, it will be appreciated by skilled workers that the basic constructs described herein may be altered to provide other embodiments that utilize products, processes, methods, and compositions of the invention with other promoters comprising inducible genes activated in inflammation such as the types listed above that exhibit similar functions that can be used to target cells at the site of infection.

The Apoptosis-Inducing Gene (which will sometimes be referred to herein as AIG) was driven by a TNFα promoter (TNFp) or other inducible gene activated in inflammation. In one embodiment, apoptosis was selectively induced in those cells capable of producing TNFα. The TNFp-AIG or other chimeric nucleic acid may be conveniently introduced in vivo using conventional gene therapy techniques. Advantageously, in the embodiment wherein the chimeric nucleic acid was TNFp-AIG, it was expressed in only those cells producing the inflammatory cytokine, TNFα. In addition, since the TNFp-AIG chimeric nucleic acid contains the TNFα promoter elements, it also sequesters inducible, TNFp-selective transcription factors. Such sequestration results in a reduction in endogenous production of TNFα. The present invention relates specifically to TNFp-AIG and similar gene constructs, cells containing chimeric nucleic acids, methods for induction of apoptosis in cells transfected with chimeric nucleic acids, pharmaceutical compositions containing chimeric nucleic acids, methods for in vitro selection of TNFα non-producer somatic cell variants within a TNFα producing cell population and the like, a method for identifying dominant negative/dominant suppressive genes responsible for inhibiting TNFα production and therapeutic methods using the chimeric nucleic acid.

To clarify the discussion below of exemplary TNFp-AIG chimeric nucleic acids of this invention, the following sequences are illustrated:

SEQ ID NO: 1 is the nucleotide sequence corresponding to the full-length, reference human TNFα promoter sequence, as published (Takashiba S., et al., Gene, 1993, 131, 307–308). Nucleotide numbers used herein refer to the numbering of this sequence.

SEQ ID NO: 2 is the native TNFα promoter sequence of the gene that was used in this invention (−1077 nucleotides from the transcription start site, TSS). There are a few differences in the sequence of the TNFp in SEQ ID NO: 1 and SEQ ID NO: 2. Such differences in the nucleotide sequences of the TNFα promoter have been reported (Takashiba S., et al., Gene, 1993, 131, 307–308).

SEQ ID NO: 3 is the native minimal TNFα promoter sequence (nucleotide −120 through −TSS), which includes at least one enhancer element (k3 site); see Pauli, U., Crit. Rev. in Eucaryotic Gene Expression, 1994, 4, 323–344; Rhoades K. L., et al., J. Biol. Chem., 1992, 267, 22102–22107; and Takashiba S., et al., Gene, 131, 307–108).

SEQ ID NO: 4 is the enhancer region 1 (ER1) of the TNFα promoter encompassing nucleotides −1005 to −905.

SEQ ID NO: 5 is the enhancer region 2 (ER2) of the TNFα promoter encompassing nucleotides −706 to −517.

SEQ ID NO: 6 is additional multiple cloning sites (MCS) genetically engineered upstream of the −120 minimal TNFα promoter in the −120pGL3 construct.

SEQ ID NO: 7 is the 3' untranslated region (3'UTR) of the TNFα gene (Nedwin, G. E., et al., *Nucleic Acid Research*, 1985, 13, 6361–6373).

SEQ ID NO: 8 is the full length Granzyme B.

SEQ ID NO: 9 is the truncated Granzyme B, devoid of the nucleotides encoding leader peptide and inactivating di-peptide.

SEQ ID NO: 10 is the full length Granzyme B, containing the nucleotides encoding the leader peptide, but devoid of the nucleotides encoding the inactivating di-peptide.

SEQ ID NO: 11 is the enhancer region 3 (ER3) of the TNFα promoter encompassing nucleotides −234 to −120.

SEQ ID NO: 12 is the enhancer region 4 (ER4) of the TNFα promoter encompassing nucleotides −234 to −65.

SEQ ID NO: 13 is the chimeric nucleic acid −706TNFpGB 3'UTR.

SEQ ID NO: 14 is the chimeric nucleic acid −1005THFpGB 3'UTR.

The elements of the TNFα promoter for preparation of chimeric nucleic acid constructs according to this invention were selected from elements, which were capable of inducing expression of a therapeutic gene driven by the TNFα promoter. These promoter elements will be referred to herein as "inducible cis elements", "cis-inducible elements" or "enhancer elements" of the TNFα promoter.

The enhancer elements may be physically linked to the minimal promoter sequence, or separated from the minimal promoter by a linker sequence which may or may not have unique restriction sites. Thus, as summarized above, enhancer elements may be attached directly, distally, proximally, or any combination thereof, to chimeric nucleic acids of the invention. These were typically constructed upstream of the promoter. Example TNFα enhancer elements are set out in SEQ ID NO: 4, SEQ ID NO: 5, SEQ ID NO: 11, and SEQ ID NO: 12; functional fragments or variants and combinations thereof may be employed. Some preferred gene constructs according to this invention include those that have multiple copies of the enhancer elements, i.e., two or more copies. Some embodiments have about 2 to 25, more narrowly 2 to 10, and even more narrowly, 2 to 5 copies.

The terms "TNF promoter", "TNFα promoter" and "TNFp" are used interchangeably herein. Unless noted to the contrary, these terms refer to the entire nucleotide sequence corresponding to a native TNFα minimal promoter sequence attached to one or more upstream enhancer elements (either present naturally i.e. native, or genetically engineered in the laboratory). Examples include, but are not limited to, SEQ ID NO: 1, SEQ ID NO: 2, and SEQ ID NO: 3, and functional fragments, variants, and mixtures of any of these. Many functional fragments and variants of these TNFα sequences and others described herein share a sequence homology of at least about 80% and in some cases over 90%, to their native and genetically engineered counterparts, but these are known to skilled workers and defined in the references cited herein.

This invention provides a novel therapeutic method comprising the step of introducing into the cells of a mammal a chimeric nucleic acid comprising an apoptosis-inducing gene (AIG) driven by the TNFα promoter (TNFp). Example chimeric nucleic acids of the invention are set out in SEQ ID NOs 13 and 14; functional fragments or variants of these may also be employed. Without wishing to be bound by theory, as a result of being controlled by the TNFp, AIG was expressed in only those cells producing the inflammatory cytokine, TNFα. Therefore, any cells expressing TNFα will be self-destructive, while cells that do not express TNFα will be unaffected. Advantageously, this methodology can target any TNFα-producing cells, such as activated macrophages, activated T-cells, macrophage-like, fibroblast-like synoviocytes and primary cells residing in RA joints. Indeed, the targeted TNFα-producing cell can be one which normally does or normally does not carry or expresses an apoptosis gene in its native, unaltered form. Therefore, using the chimeric nucleic acids and methods of this invention, the cellular sources of TNFα can be destroyed in a highly selective manner.

Another advantage of using the TNFp-AIG chimeric nucleic acid of this invention was that TNFp sequesters transcription factors needed by endogenous TNFp, thereby leading to a reduction in endogenous TNFα production. In one example, TNFp was present in the therapeutically targeted cell in vast excess. This may be accomplished by introducing multiple copies of the transfected gene into the cell. Alternatively, the TNFp-AIG chimeric nucleic acid according to this invention can contain multiple copies of the inducible cis elements of the TNFα promoter. As mentioned above, multiple copies of the "inducible enhancer elements" of TNFp are present in some embodiments of the TNFp-AIG chimeric nucleic acids of this invention. By including multiple copies of the inducible cis elements of the TNFp construct, the transcriptional factors needed by the transfected cell to produce TNFα were sequestered by the exogenously introduced sequence. This preferred chimeric TNFp-AIG construct was characterized by an increased effectiveness in competing for the TNFp-specific transcription factors as compared to chimeric nucleic acids of this invention containing only a single enhancer element linked to TNFp. The "inducible super promoter" constructed in this way was capable of (1) more effectively competing for TNFα specific inducible transcription factors and (2) driving expression of the apoptosis inducing gene in an augmented fashion by virtue of multiple enhancing elements.

In rheumatoid arthritis patients, synovectomy, i.e., removal of synovial tissue, has been shown to be clinically beneficial. Unlike conventional and surgical synovectomy procedures, the cell-targeted therapeutic method described herein targets only cells producing TNFα. Thus, advantageously, the introduction and expression of the TNFP-AIG chimeric gene and subsequent induction of apoptosis do not induce an inflammatory response. Accordingly, methods of this invention were comparatively selective and result in minimal tissue damage and a reduction in inflammation.

The products and methods described herein are useful for the treatment of other inflammatory disorders as well. Such inflammatory disorders include, but are not limited to, multiple sclerosis, Guillain-Barre syndrome, Crohn's disease, ulcerative colitis, psoriasis, graft versus host disease, lupus erythematosus, insulin-dependent diabetes mellitus, psoriatic arthritis, sarcoidosis, hypersensivity pneumonitis, ankylosing spondylitis and related spoldyloarthropathies, Reiter's syndrome and systemic sclerosis. Thus, this invention encompasses methods for treating an inflammatory disorder in a patient administering to a patient in need of such treatment a pharmaceutically effective amount of a pharmaceutical composition having the chimeric nucleic acid according to the invention. Apoptosis was induced in inflammatory cells or cells at a site of inflammation of the patient by introducing into the cells at least one chimeric nucleic acid of the invention. This was typically accomplished by preparing a pharmaceutical composition containing at least one chimeric nucleic acid of the invention and typically a pharmaceutically acceptable carrier, and administering the composition to a patient using standard means known to those skilled in the art. The pharmaceutical composition can be delivered directly to the site of inflammation using local topical, intravenous, intraperitoneal, and similar methods. Further methodology discussed below.

In addition to the therapeutic indications, the chimeric nucleic acids according to this invention can be used in a variety of useful screening and selection methods. In one such method, TNFα non-producer somatic cell variants within a TNFα producing cell population can be selected in vitro by introducing a TNFp-AIG chimeric nucleic acid into the TNFα producing cell population. Cells producing TNFα will undergo apoptosis. Cells that do not produce TNFα will survive. Selection of those cell variants possessing the survival phenotype was an easy way to identify TNFα non-producer cells. Such a selection process may be used to determine expression of genes that act in-trans to regulate activity of the TNFα promoter, thereby reducing TNFα production. Such genes were characterized as dominant negative (DN)/dominant suppressive genes in other systems (Behrends S., et al., *J. Biol. Chem.* 1995, 270, 21109–21113; Zhang S., et al., *J. Biol. Chem.*, 1995, 270, 23934–23936; Watowich S. S., et al., *Mol. Cell Biol.*, 1994, 14/6, 3535–3549).

In a further in vitro method, a TNFp-AIG chimeric nucleic acid according to this invention can be used to identify dominant negative gene responsible for the genesis of a TNFα non-producing cell population. According to this method, a TNFp-AIG chimeric nucleic acid according to this invention was introduced into cells that produce TNFα. Barring the presence of a dominant negative gene, those cells should undergo apoptosis upon activation. Therefore, it can be deduced that surviving variants possess a dominant negative gene capable of down-regulating TNFα production. The dominant negative gene can be readily identified by producing a cDNA library and transfecting cell lines (e.g., Jurkat and THP-1). These cells were either stable transfectants of an inducible TNFp-AIG chimeric nucleic acid or TNFp-luciferase gene TNFp-AIG transfected cells will be selected for the survival phenotype following in vitro activation; survival phenotype was indicative of the effect of the DN genes. In the cells transfected with TNFp-luciferase gene, reduction in the luciferase activity will be indicative of the DN gene effect. Dominant negative genes identified using this protocol can be used as the future therapeutic agents themselves. Such genes will be the candidates for gene therapy in order to reduce TNFα production.

The methods utilized for gene transfer were grouped into two broad categories:
1. Direct approach: In situ transduction of the therapeutic gene into target cells such as synoviocytes using a suitable vector as a carrier for the therapeutic gene. The vector containing therapeutic gene was injected directly into the affected area (e.g., an arthritic joint).
2. Indirect approach: Ex-vivo transfection of the therapeutic gene into target cells such as synoviocytes. In this approach, the synovium was removed from joints, synoviocytes were isolated and cultured in vitro. In vitro cultured cells were transfected with the therapeutic gene, and genetically modified synoviocytes were transplanted back into the synovium.

For in vivo transfer, several vectors have been evaluated for their efficacy in gene delivery (Nita, et al., *Arthritis & Rheumatism*, 1996, 39/5, 820–828). Among the vectors used for gene therapy, the vectors derived from retroviruses were by far the best developed. They were able to insert genetic material in the host genome and produce stable transfectants. These vectors, however were unable to infect non-dividing cells and, since they were inserted in the host genome, the possibility of insertional mutagenesis cannot be ruled out. In comparison, the vectors derived from adenoviruses infect dividing as well as non-dividing cells and deliver DNA episomally. The disadvantage of adenovirus based vectors was that these vectors continue to produce viral proteins in infected cells making them potentially antigenic. A third type of viral based vectors was derived from Herpes simplex viruses (HSV), which were also capable of infecting dividing as well as non dividing cells.

Among the non-viral vector systems, cationic liposomes and naked plasmid DNA have been evaluated. Liposomes were at the most advanced stage of development, although certain types of cells such as muscle and skin take up, retain and express naked plasmid DNA.

Particle-mediated gene-delivery system is also possible (Rakhmilevich, et al., *PNAS*, 1996, 93, 6291) and is a promising approach.

The following "in vivo" gene delivery protocols can be used to deliver the chimeric nucleic acids of this invention:
(1) Nita et al., *Arthritis and Rheumatism*, 1996, 39, 820–823
  In vivo experiment in rabbits:
  Each vector was injected intra-articularly into one knee joint. For viral vectors, between $10^8$ and $10^9$ particles suspended in 0.5 ml balance salt solution were injected per knee.
  Liposome-DNA complexes (200 nroles of DC-Chol complexed with 20 μg of DNA/ml) in 1 ml balance salt solution were injected per knee.
(2) *Methods in Molecular Medicine: Gene Therapy Protocols*, Paul Robbins, ed., 1997, Barr et al., pages 205–212
  Adenovirus-based vector delivery to hepatocytes: Rat hepatocytes $1\times10^{11}$ PFU in 100 g animal.
  In dogs (12–17 kg), portal vein was perfused with about $1.5\times10^{11}$ PFU/kg gives 1 adenovirus genome copy per diploid copy of host DNA.
  In rabbits (2–4kg), $1.5\times10^{13}$ virus particles (about $1.5\times10^{11}$ PFU) gives 100% hepatocyte transduction; $4\times10^{12}$ virus particles give 50–75% transduction.
Yang N-S, et al., 281–296
  Gold particle-mediated gene delivery: Transfection of mammalian skin tissue- 0.1, 0.5, 1.0 and 2.5 μg of DNA/mg particle gives linear relationship with transgene expression levels.
Nabel, et al., 297–305
  Liposome-mediated gene delivery in humans:
    Protocol 1: 15 nmol DC-Chol/Dope liposomes combined with 1 μg DNA in 0.7 ml. 0.2 ml of the above mixture was injected into the patient's melanoma nodule. For catheter delivery, 0.6 ml of the solution was delivered into the artery.
    Protocol 2: 15nmol DMRIE/Dope liposomes combined with 5 μg DNA in 1.0 ml.
  For direct intra-tumor injections, DNA concentrations range from 3 μg complexed with 4.5 nM DMRIE/Dope to 300 μg complexed with 450 nM DMRIE/Dope.

(3) Roessler, et al. 369–374
Gene transfer to synovium:
A range of doses, $10^9$–$10^{12}$ adenovirus particles containing therapeutic gene/joint were used. However, the optimal dose for any particular experimental series needs to be determined empirically, and was dependent on both the properties of the recombinant adenoviral genomic backbone being used as well as the transgene being expressed.

For the indirect approach, a variety of methods were well established, including utilization of cationic lipid or cationic polymer-based transfection and electroporation.

Any of the above-referenced techniques can be altered to suit the particular needs of those of ordinary skill in the art. Such modifications are well within the level of skill possessed by ordinary practitioners and do not require undue experimentation. These obvious variations are within the scope of this invention.

EXAMPLES

In order that this invention be more fully understood, the following examples are set forth. These examples are for the purpose of illustrating some preferred embodiments of this invention, and are not to be construed as limiting the scope of this invention in any way.

Example 1

Production of TNFp-Granzyme B Constructs

In order to construct chimeric Granzyme B driven by the enhancer cis elements of the TNF promoter, either in a single or multiple copies of the same region or various regions, identification of the regions of interest responsible for optimal inducible expression of the reporter gene was performed.

Selection of the TNFα Promoter Elements for Constructing a Chimeric Nucleic Acid.

Figure 3:
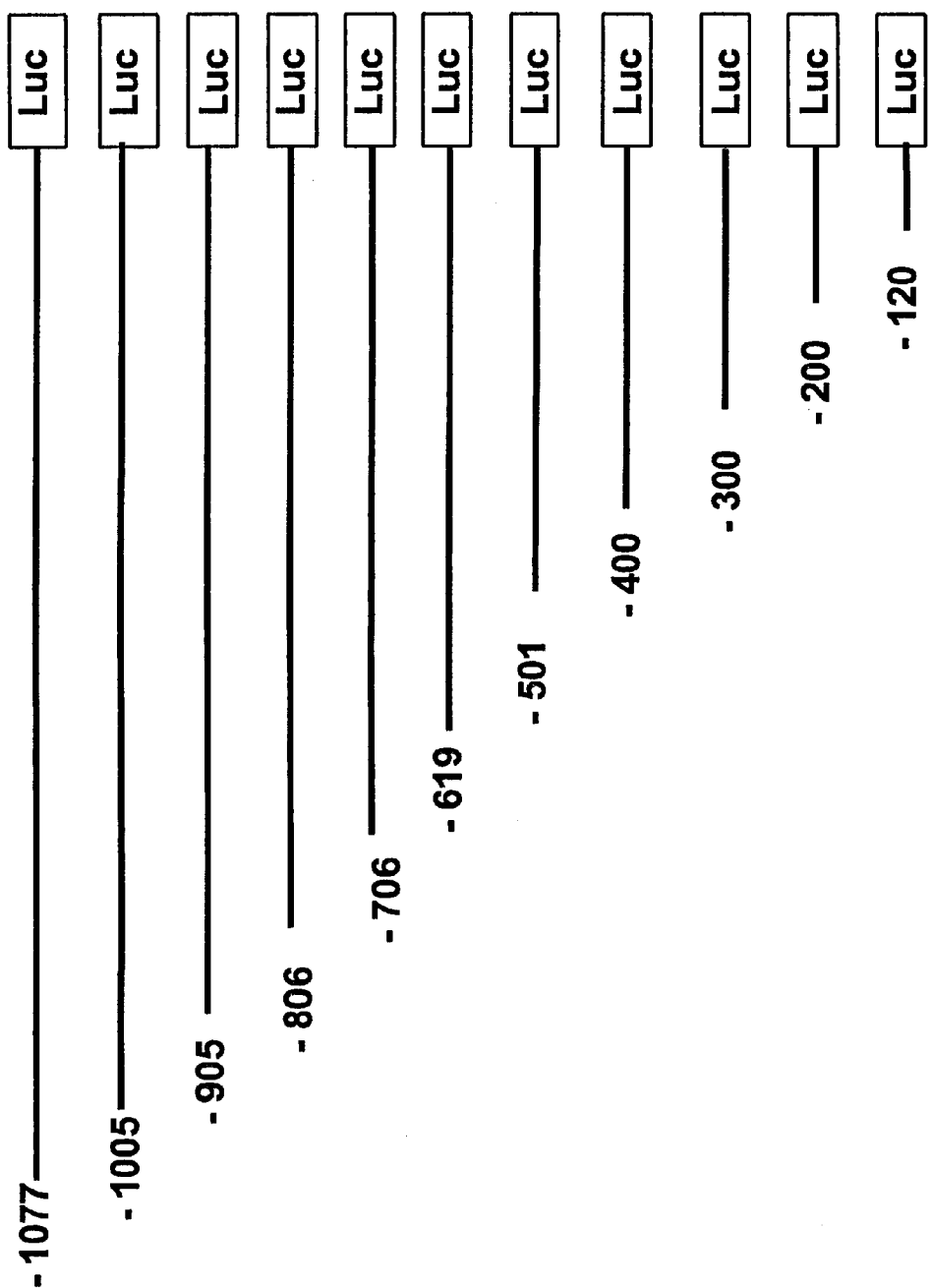
FIG. 3 is a summary of deletion constructs used for identification of the inducible cis elements of the TNFα promoter using luciferase gene (Luc) expression as the reporter system.
Figure 4A:
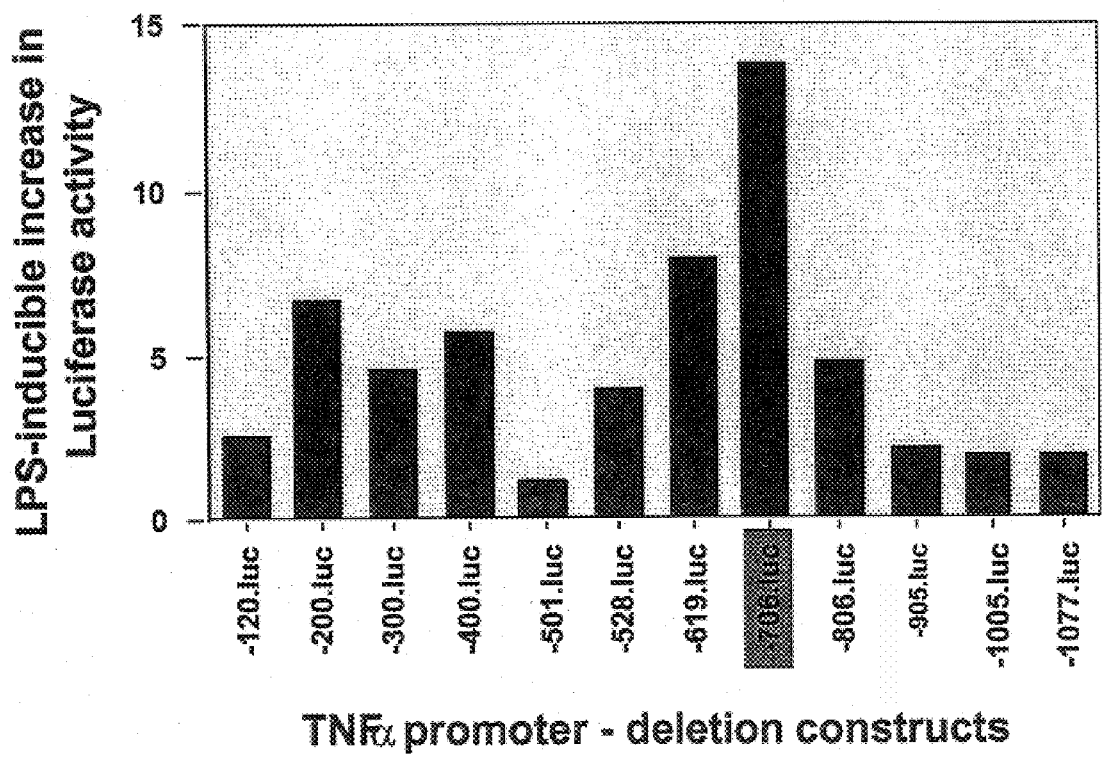
FIG. 4(a) shows results of the representative experiment performed to assess expression of luciferase gene driven by deletion constructs of the TNFα promoter in transiently transfected Jurkat Cells. Histograms represent stimulation index as a measure of inducibility by activating agent PMA. Jurkat cells produce TNFα following stimulation with PMA.

The regions of the TNFα promoter were amplified by polymerase chain reaction (PCR) using primers encompassing various deletion constructs of the TNFα promoter (FIG. 3). The regions identified by other investigators in various other cellular systems were used as reference (Rhoades, et al., *J. Biol. Chem.*, 1992, 267, 22102–22107; Leitman, et al., *Mol. Cell Biol.*, 1992, 12, 1352–1356; Pauli U., *Crit. Reviews Eukaryotic Gene Expression*, 1994, 4, 323–344). The PCR-amplified genes were then cloned upstream of a reporter gene, such as luciferase, in a commercially available promoterless vector. These constructs were tested for their constitutive and inducible expression in various cell lines such as Jurkat (T lymphoblastoid), U973 (myelomonocytic), THP-1 (monocytic), fibroblasts and in vitro cultured human synoviocytes. Identification of the regions responsible for inducible expression of the reporter gene was primarily based on the results obtained using two TNFα-producing cell lines, viz. Jurkat (following stimulation with PMA) and THP-1 (following stimulation with LPS) (FIG. 4a and b). These cells were transiently transfected by using well established methods and commercially available reagents, e.g., DEAE dextran and Superfect. The cis-elements of the TNFα promoter that were responsible for inducible expression of the reporter gene were then used for constructing TNFp-Granzyme B chimeric nucleic acids.

Construction of TNFp-Granzyme B Chimeric Nucleic Acids.

Figure 5:
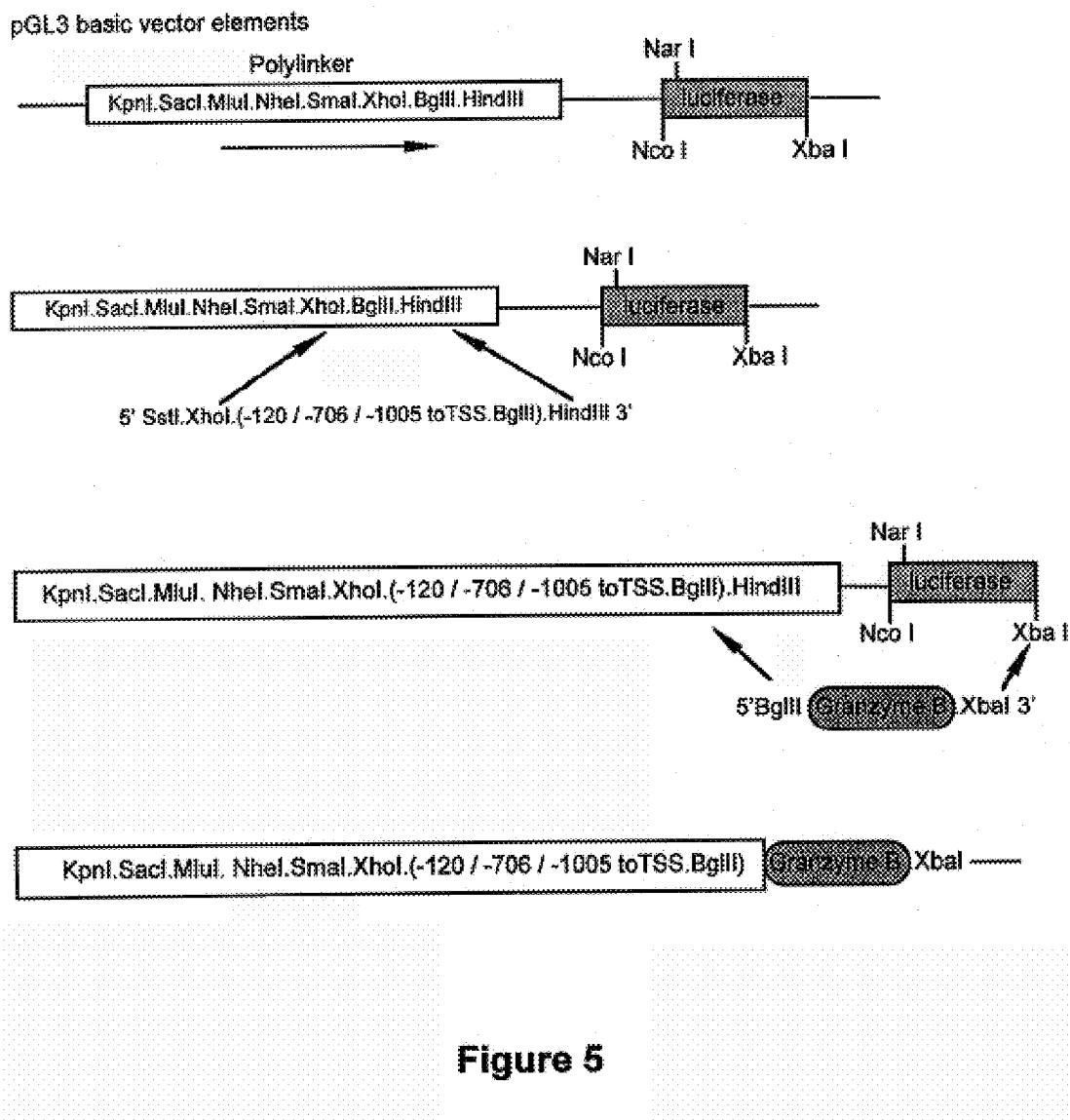
FIG. 5 is a flow chart for preparation of the TNFpGB using selected native elements of the TNFα promoter and Granzyme B.

Granzyme B coding region was amplified using oligo-dT-primed cDNA as a template, which was obtained from PHA/anti-CD3-activated human peripheral blood lymphocytes that were maintained in IL-2 containing medium. Sense primers corresponding to codons 1–7, and 21–27 were used for amplification of full length (SEQ ID NO: 8) or truncated (SEQ ID NO: 9) forms of Granzyme B. Anti-sense primer used was same in both amplifications to give products corresponding up to stop codon, i.e. residue 248. Di-peptide deleted Granzyme B constructs (SEQ ID NO: 10) were prepared using full length Granzyme B (SEQ ID NO: 8) as a template. Mutagenic sense and antisense complementary primers, flanking 15 nucleotides on either sides of, but not including, the six nucleotides corresponding to codons 19 and 20 (inactivating di-peptide) were used to create deletion. The constructs were made using Quick-Change mutagenesis kit (Stratagene). Nucleic acid fragments encoding di-peptide-deleted Granzyme B were subcloned downstream of the TNFα promoter by replacing the luciferase gene in the deletion constructs −706 and −1005 of the TNFα promoters (FIG. 5). The entire 3' untranslated region of the TNFα gene (SEQ ID NO: 7) was PCR-amplified and was inserted downstream of the nucleic acid fragment encoding di-peptide deleted Granzyme B gene driven by −706 and −1005 deletion fragments of the TNFα promoter. The entire sequence of the chimeric nucleic acids is in SEQ ID NO: 13 and 14.

Construction of TNFα Super Promoter-Granzyme B Chimeric Nucleic Acids.

Figure 4B:
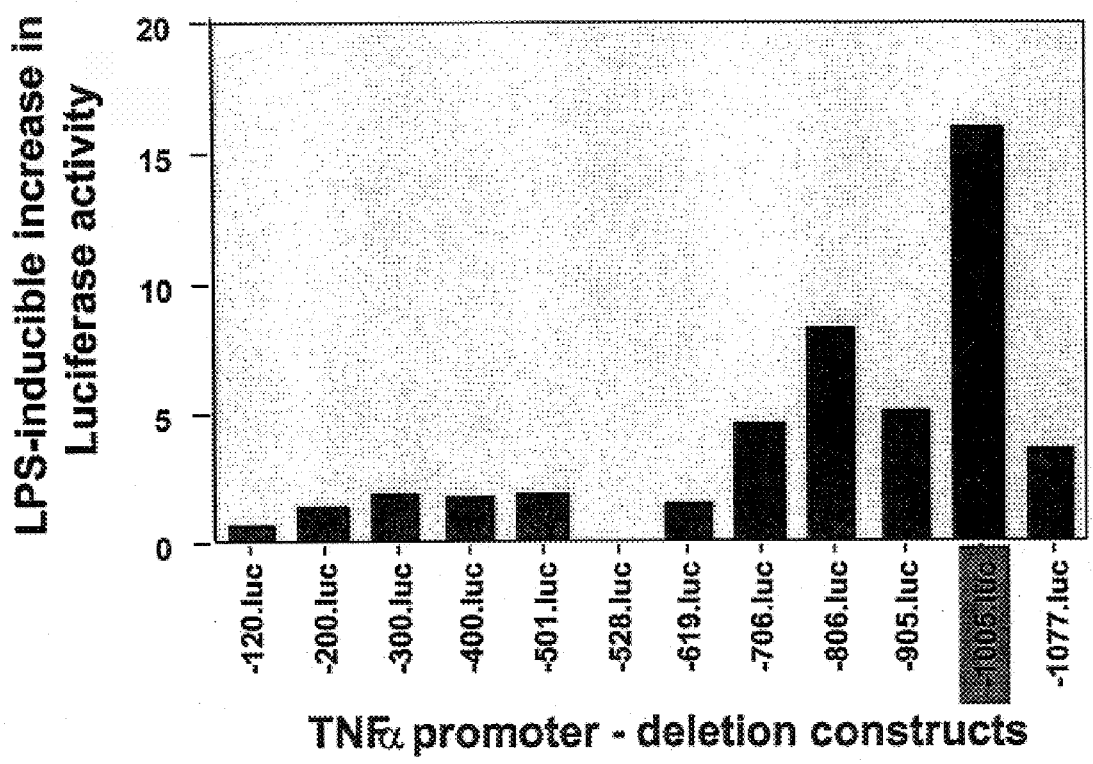
FIG. 4(b) Results of the representative experiment performed to assess expression of luciferase gene driven by deletion constructs of the TNFα promoter in transiently transfected THP-1 Cells. Histograms represent stimulation index as a measure of inducibility by activating agent, LPS. THP-1 cells produce TNFα following stimulation with LPS.
Figure 7:
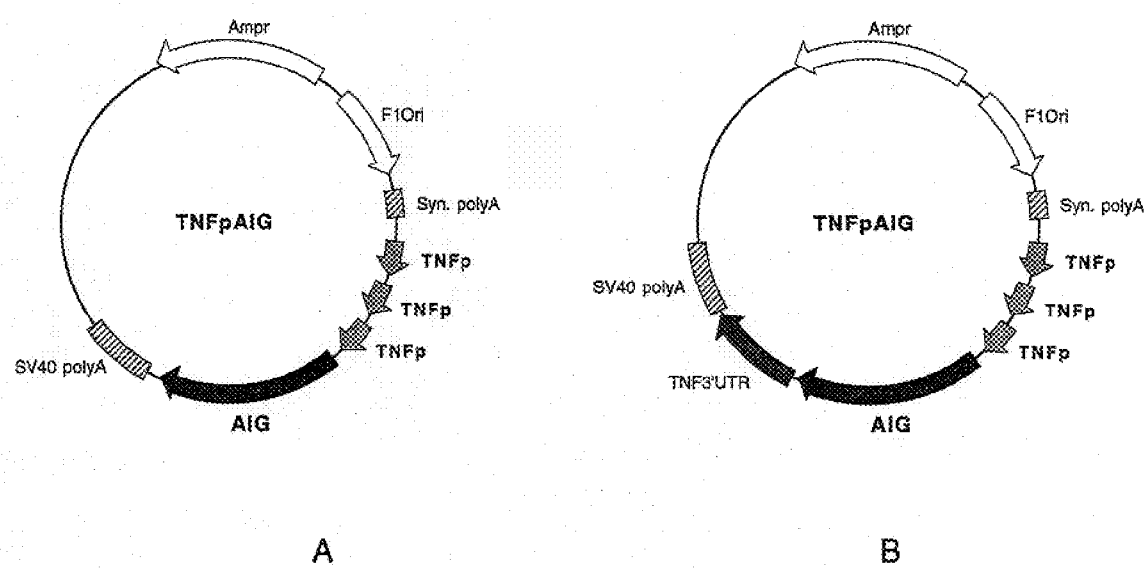
FIG. 7 (a and b) is a diagrammatic representation of a TNFp-AIG chimeric nucleic of this invention, comprising multiple copies of the inducible cis elements of the TNFα promoter which, in turn, drive expression of the AIG (FIG. 7a). A diagrammatic representation of a TNFpAIG chimeric nucleic acid, comprising multiple copies of the inducible cis elements of the TNFα promoter, driving expression of the AIG, downstream of which are 3' untranslated region of the TNFα gene (TNF3'UTR) (FIG. 7b). 3'UTR of the TNFα gene was implicated in the regulation of the inducible expression of TNFα (Han, J., et al., *J. Immunology*, 1991, 146, 1843–1843, Crawford, E. K., et al., *J. Biol. Chem.*, 1997, 272, 21120–21137, and FIG. 9).

Two broad preferred regions, viz., ER1(−1005 to −905) (SEQ. ID NO: 4), ER2(−706 to −517) (SEQ ID NO: 5), of the TNFα promoter, containing elements responsible for inducible expression of the reporter gene described above (FIG. 4a and 4b) were PCR amplified and were ligated upstream of the minimal native promoter (−120 through TSS, SEQ ID NO: 3), either as a single copy or multiple copies. Two more regions ER3(−234 to −120) (SEQ. ID NO: 11), and ER4(−234 to −65) (SEQ. ID NO: 12) of the TNFα promoter were also identified as enhancer regions which were employed in the chimeric constructs using the strategies described below. The super promoter contains multiple (2–10) cassettes of the above mentioned regions containing inducible promoter elements (FIG. 7). This was achieved by PCR amplifying the regions of interest using primers synthesized with restriction sites inserted at the 5' end of each of the primers. These unique restriction sites flank the amplified gene product of interest. Preferably, PCR amplified AIG was cloned downstream of the TNFα super promoter, replacing the luciferase reporter gene in the original construct as described (FIG. 5) for the native TNFα promoter.

Figure 8A:
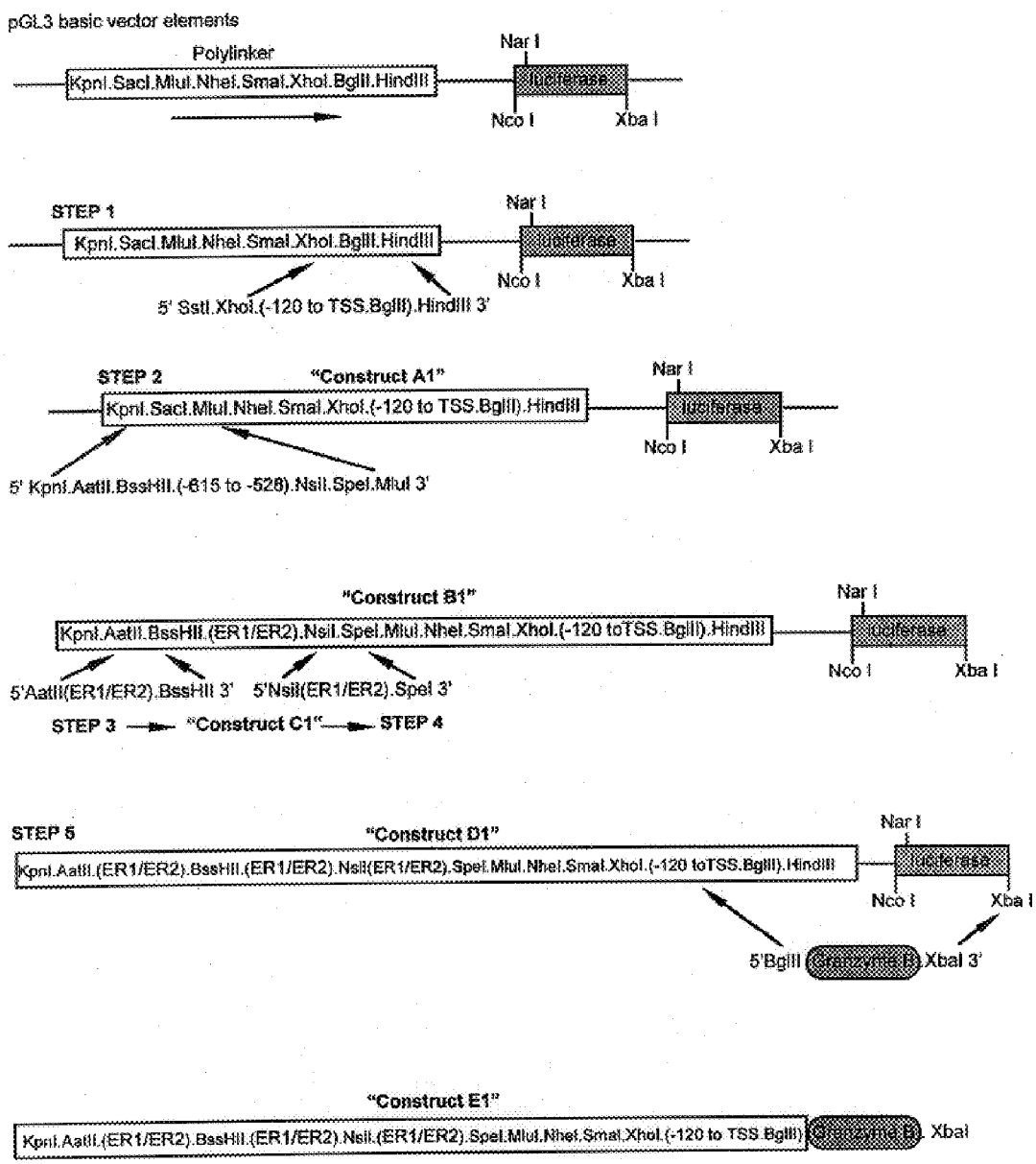
FIG. 8 (a and b) are flow charts of schemes for preparing TNFα super-promoter-Granzyme B chimeric constructs.
Figure 8B:
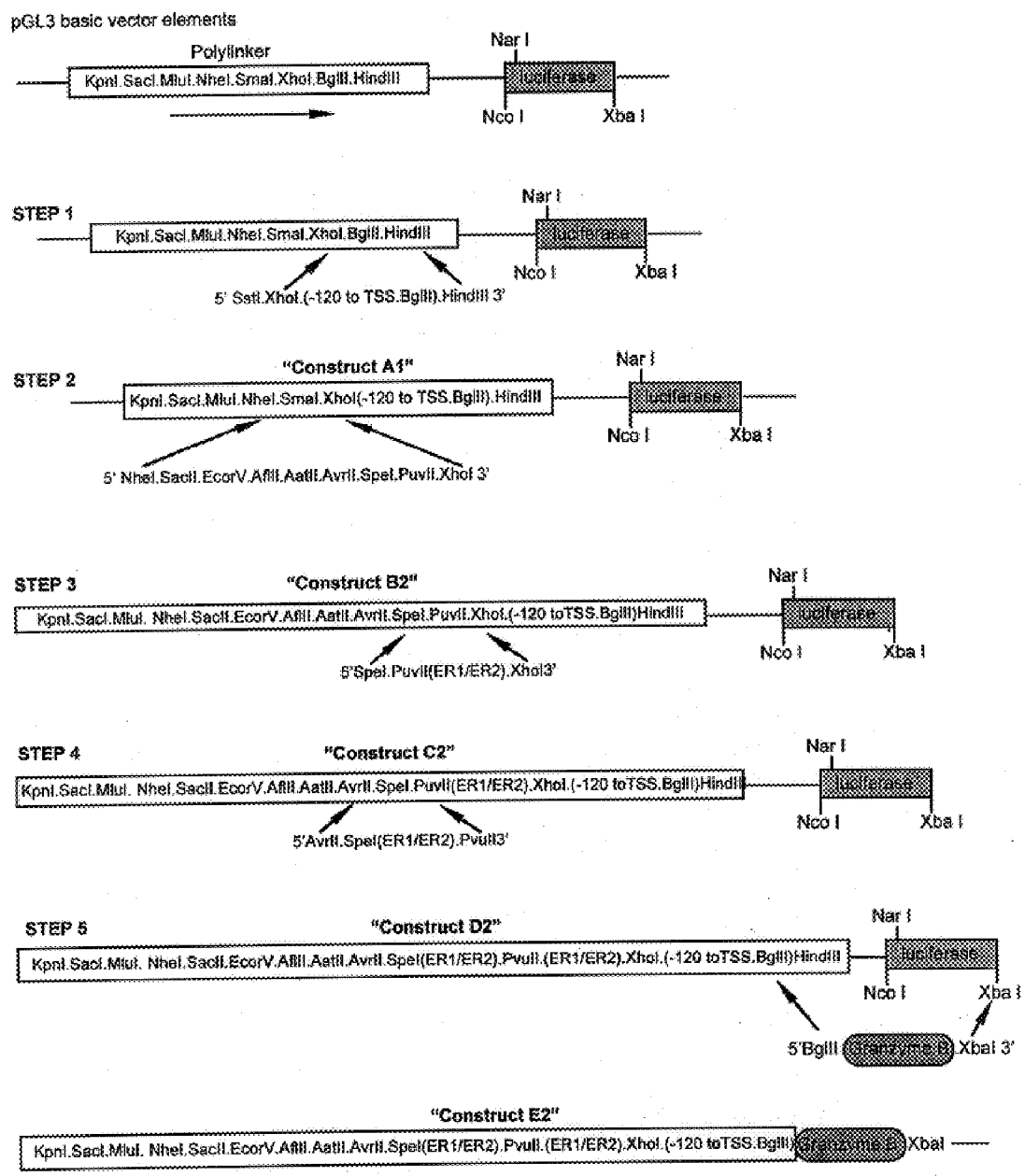

The schemes for construction of a TNFα super promoter and the linker sequences representing unique restriction sites (these restriction sites were absent in the selected elements of the TNFα promoter and Granzyme B) for efficient directional insertion was outlined below and depicted in FIG. 8:

Scheme 1:
STEP 1: Insertion of the TNFα minimal promoter (−120 to TSS) into the pGL3 basic (promoterless) luciferase vector (Promega):

The elements of pGL3 basic vectors that were used for construction of the chimeric nucleic acid TNFp-AIG are shown below.

__KpnI.SacI.MluI.NheI.SmaI.XhoI.BglII.HindIII. [luciferase].XbaI__

The minimal promoter was PCR amplified using primers containing XhoI and BglII.HindIII sites, so that XhoI was at the 5'end and BglII.HindIII sites were at the 3' end of the amplified product. This fragment was inserted into the polylinker of the pGL3 basic vector using these same restriction sites. This construct was referred to as "Construct A1" and was as follows:

__KpnI.SacI.MluI.NheI.SmaI.XhoI.(−120 to TSS BglII) .HindIII.[luciferase].XbaI__

STEP 2: The enhancer fragment (ER1, ER2, ER3, or ER4) was PCR amplified using the primer containing several restriction sites. The resulting fragment will have restriction sites KpnI.AatII.BssHII at the 5' end and NsiI.SpeI.MluI at the 3'end as follows:

5' KpnI.AatII.BssHII.(ER1, ER2, ER3, or ER4).NsiI.SpeI.MluI 3". The fragment was inserted into the "Construct A1" generated in STEP 1 using KpnI and MluI restriction sites. This construct was referred to as "Construct B1" and was as follows:

_KpnI.AatII.BssHII.(ER1, ER2, ER3, or ER4).NsiI.SpeI.MluI.NheI.SmaI.XhoI(−120 to TSS BglII).HindIII.[luciferase].XbaI_

STEP 3: The TNFα enhancer fragment (ER1, ER2, ER3, or ER4) was amplified using the primers containing restriction sites AatII and BssHII to generate the PCR product as follows:

5' AatII.(ER1, ER2, ER3, or ER4).BssHII 3'. This fragment was cloned into the "Construct B1" using these same restriction sites. This construct was referred to as "Construct C1" and was as follows:

_KpnI.AatII.(ER1 or ER2).BssHII.(ER1, ER2, ER3, or ER4).NsiI.SpeI.MluI.NheI.SmaI.XhoI(−120 to TSS BglII).HindIII.[luciferase].XbaI_

STEP 4: The TNFα enhancer fragment (ER1, ER2, ER3, or ER4) was amplified using the primers containing restriction sites NsiI and SpeI to generate the PCR product as follows:

5' NsiI.(ER1, ER2, ER3, or ER4).SpeI 3'. This fragment will be cloned into the "Construct C1" using these same restriction sites. This construct was referred to as "Construct D1" and was as follows:

_KpnI.AatII.(ER1, ER2, ER3 or ER4).BssHII.(ER1, ER2, ER3, or ER4).NsiI.(ER1, ER2, ER3, or ER4).SpeI.MluI.NheI.SmaI.XhoI(−120 to TSSBglII).HindIII.[luciferase].XbaI STEP 5: Granzyme B coding regions were PCR-amplified using the primers containing BglII and XbaI restriction sites generating the fragment as follows: 5' EcoRI.BglII.[Granzyme B].XbaI 3". This fragment was inserted into the "Construct D1" using BglII and XbaI. The resulting construct was referred to as "Construct E1" and was as follows:

_KpnI.AatII.(ER1, ER2, ER3, or ER4).BssHII.(ER1, ER2, ER3, or ER4).NsiI.(ER1, ER2, ER3, or ER4).SpeI.MluI.NheI.SmaI.XhoI(−120 to TSS.BglII).[Granzyme B].EcoRI.XbaI_

Alternatively scheme 2 was followed:

Scheme 2:

STEP 1: Same as in scheme 1 giving rise to "Construct A1", which was as follows:

KpnI.SacI.MluI.NheI.SmaI.XhoI.(−120 to TSS BglII).HindIII.[luciferase].XbaI

STEP 2: Insertion of additional Multiple Cloning Sites (SEQ ID NO: 6).

Two complementary oligonucleotides (5' phosphorylated) providing

_NheI.SacII.EcoRV.AflII.AatII.AvrII.SpeI.PvuII.XhoI_ were synthesized using commercial sources. These oligonucleotides were annealed and then cloned into NheI and XhoI sites of the "Construct A1". The resulting construct referred to as "Construct B2" and it was as follows:

_KpnI.SacI.MluI.NheI.SacI.EcoRV.AflII.AatII.AvrII.SpeI.PvuII.XhoI.(−120 to TSS BglII).HindIII.[luciferase].XbaI_

STEP 3: The TNFα enhancer fragment (ER1, ER2, ER3, or ER4) was amplified using the primers containing restriction sites SpeI.PvuII at the 5' end, and XhoI at the 3' end to generate the PCR product as follows: 5' SpeI.PvuII.(ER1, ER2, ER3, or ER4).XhoI 3'. This fragment was cloned into the "Construct B2" using SpeI and XhoI restriction sites. This construct was referred to as "Construct C2" and was as follows:

_KpnI.SacI.MluI.NheI.SacII.EcorV.AflII.AatII.AvrII.SpeI.PvuII.(ER1, ER2, ER3, or ER4).XhoI.(−120 to TSS BglII).HindIII.[luciferase].XbaI_

STEP 4: The TNFα enhancer fragment (ER1, ER2, ER3, or ER4) was amplified using the primers containing restriction sites AvrII.SpeI at the 5' end, and PvuII at the 3' end to generate the PCR product as follows: 5' AvrII.SpeI.(ER1, ER2, ER3, or ER4).PvuII 3'. This fragment was cloned into the "Construct C2" using AvrII and PvuII restriction sites. This construct was referred to as "Construct D2" and was as follows:

_KpnI.SacI.MluI.NheI.SacII.EcorV.AflII.AatII.AvrII.SpeI.(ER1, ER2, ER3, or ER4).PvuII.(ER1, ER2, ER3, or ER4).XhoI.(−120 to TSS BglII).HindII.[luciferase].XbaI_

Thus, using this strategy at least seven copies of the enhancer regions (ER1, ER2 ER3, or ER4 individually or in combination), one at a time, can be added by using one more restriction site upstream of the previous one in PCR amplification of the enhancer regions of choice. Once the desired number of copies of the enhancer regions were added, AIG was inserted downstream of the super promoter as described in the STEP 5 of the scheme 1.

The inducible expression of the chimeric TNFp-Granzyme B gene was tested by transient transfection of the cell lines mentioned above. The expression of TNFp-Granzyme B nucleic acid was measured by detecting apoptosis of transfected cells, assessing AIG expressed proteins in Western blots using commercially available antibodies and assessing protease activity using commercially available, well documented specific synthetic tetrapeptide substrate.

Regulation of the TNFp-driven Expression of a Reporter Gene.

The 3' untranslated region of the TNFα gene plays an important role in regulation of the TNFα biosynthesis. It was involved in translational expression of the TNFα gene in normal, non-activated states. Importantly, these elements allow de-repression to occur when TNFα-producing cells were activated by external stimuli (Han, J., et al., *J. Immunology*, 1991, 146, 1843–1848; Crawford, F. K., et al., *J. Biol Chem.*, 1996, 271, 22383–22390).

Figure 6A:
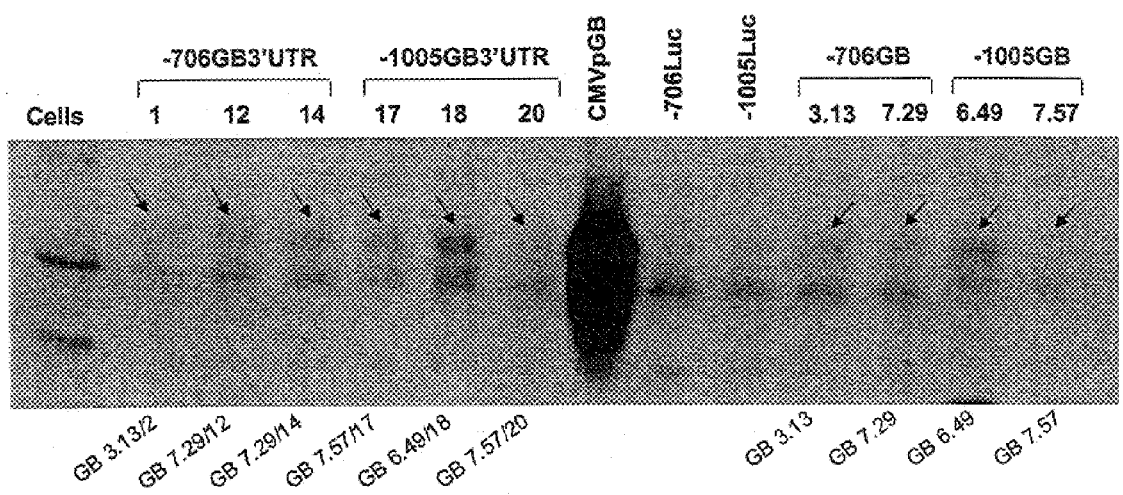
FIG. 6 (a and b) provide a summary of results from representative experiments performed to see expression of the chimeric TNFp-Granzyme B (TNFpGB). Expression of various clones of TNFpGB constructs are expressed in transiently-transfected Jurkat cells (FIG. 6a) The expression of Granzyme B was assessed by Western blot analysis using anti Granzyme B antibody. Bands representing Granzyme B in transfected cells are identified by arrows. Induction of apoptosis by expression of TNFpGB chimeric nucleic acids was assessed by transient transfection in Jurkat cells (FIG. 6b). Apoptosis was assessed by Cell Death ELISA. In both experiments, histograms with sparse dots represent non-stimulated control, where cells were transfected with a chimeric nucleic acid shown and transfected cells were not stimulated with PMA. Solid histograms represent induction of apoptosis following stimulation with PMA, either in the control transfections (transfected with −1005Luc3'UTR) or chimeric nucleic acids expressing Granzyme B.
Figure 6B:
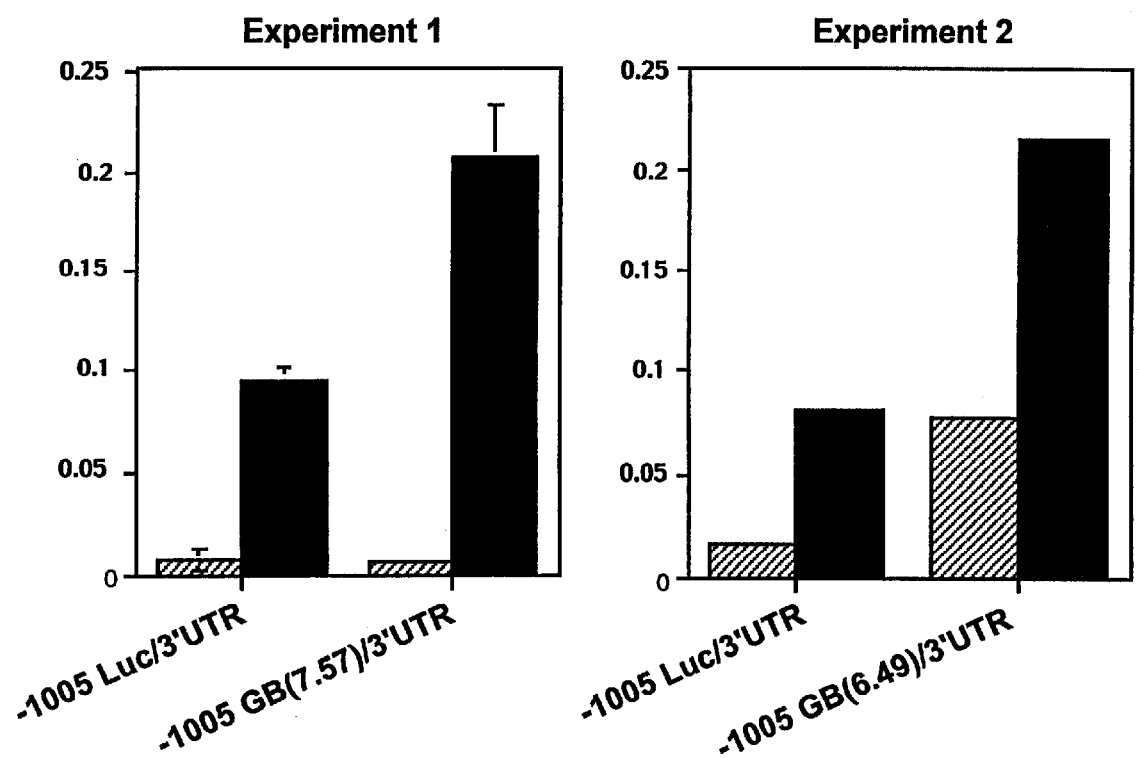
Figure 9:
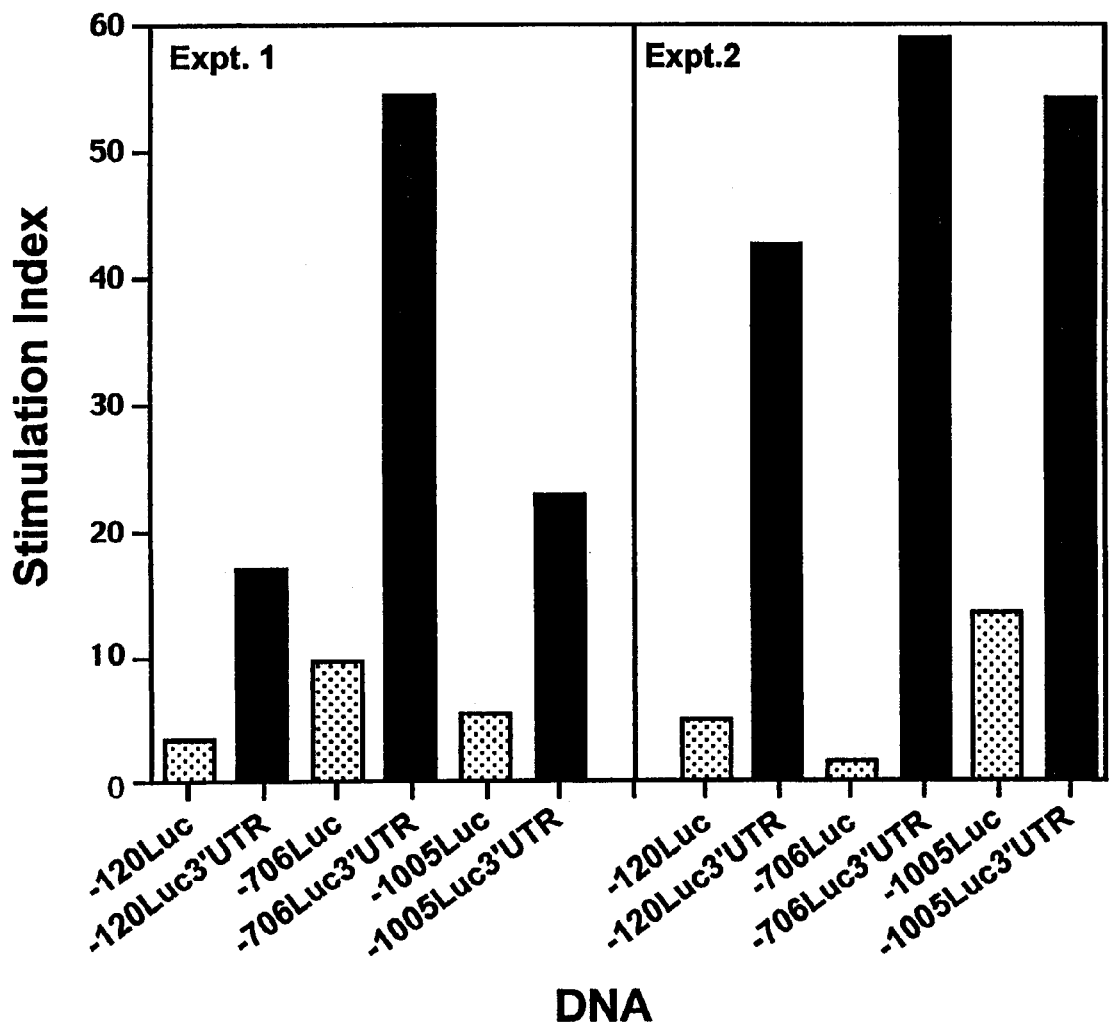
FIG. 9 shows a summary of the results of two experiments to show the regulatory effect of the TNF3'UTR on inducible expression of the luciferase reporter gene. The transient transfection was performed in a fibroblast cell line. Dotted histograms represent inducibility of TNFpLuc in the absence of TNF3'UTR and solid histograms represent inducibility of TNFpLuc in the presence of TNF3'UTR. Similar results are obtained in the Jurkat cell.
Figure 10:
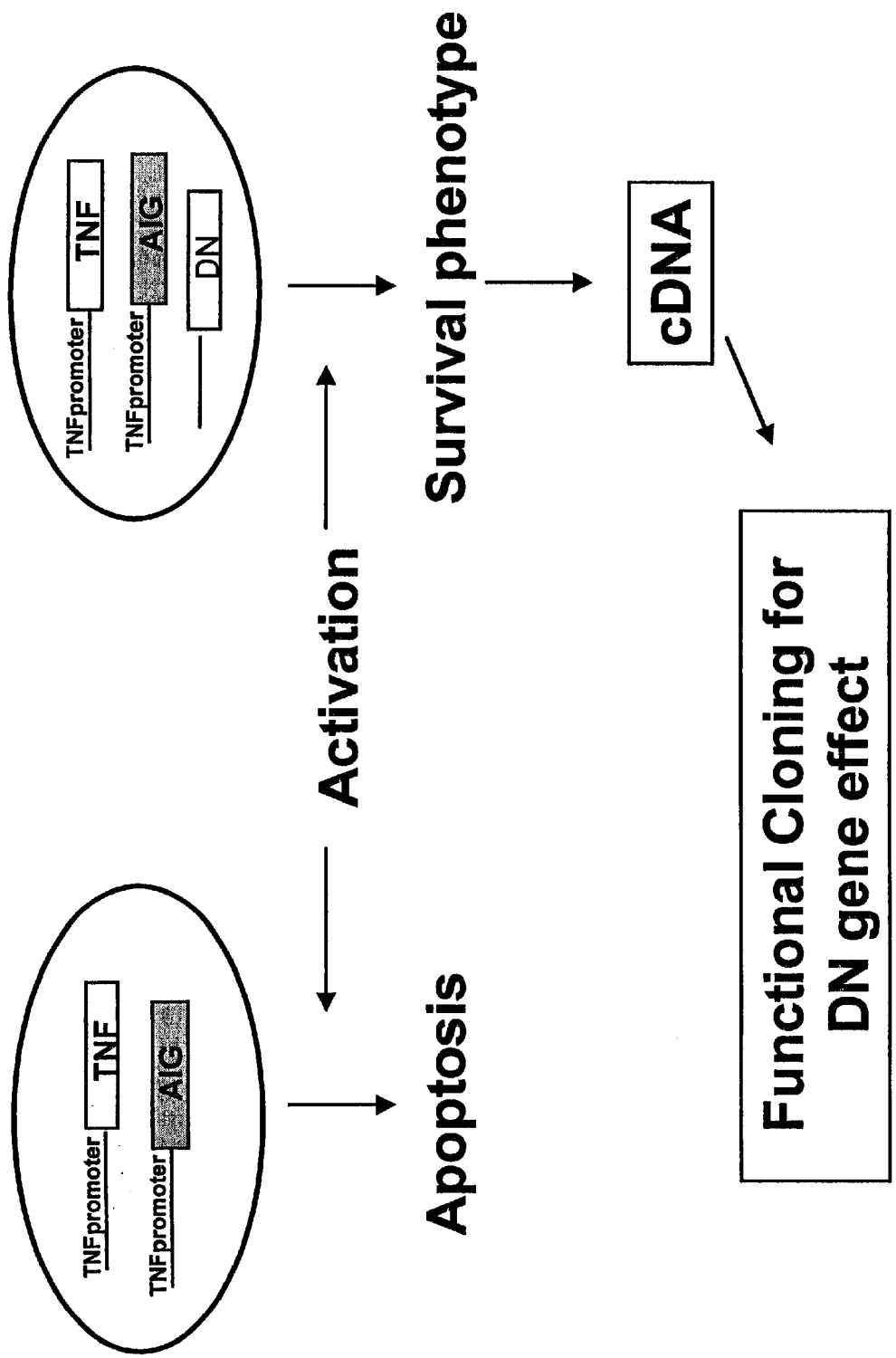
FIG. 10 is a diagrammatic representation for the selection of TNFα non-producer somatic cell variants within a TNFα-producing cell population and identification of dominant negative suppressive genes responsible for inhibiting TNFα production.
Figure 11A:
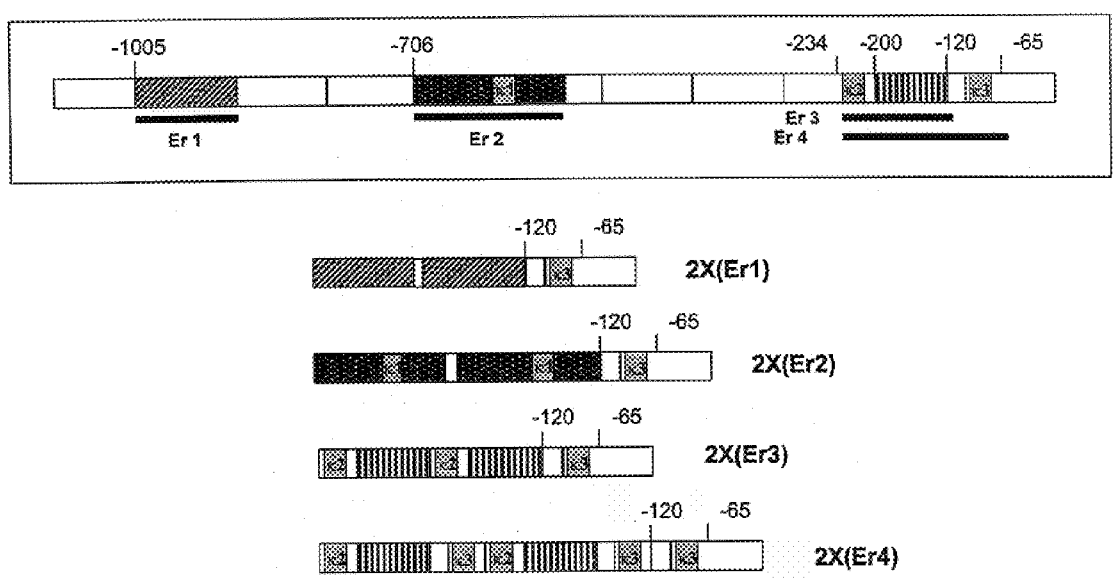
FIG. 11(a) is a diagrammatic representation of the identified Enhancer Regions (ER) ER1 (SEQ ID NO: 4), ER2 (SEQ ID NO: 5), ER3 (SEQ ID NO: 11) and ER4 (SEQ ID NO: 12) of the TNFα promoter and insertion of two copies of said ER upstream of the native −120 TNFα promoter.
Figure 11B:
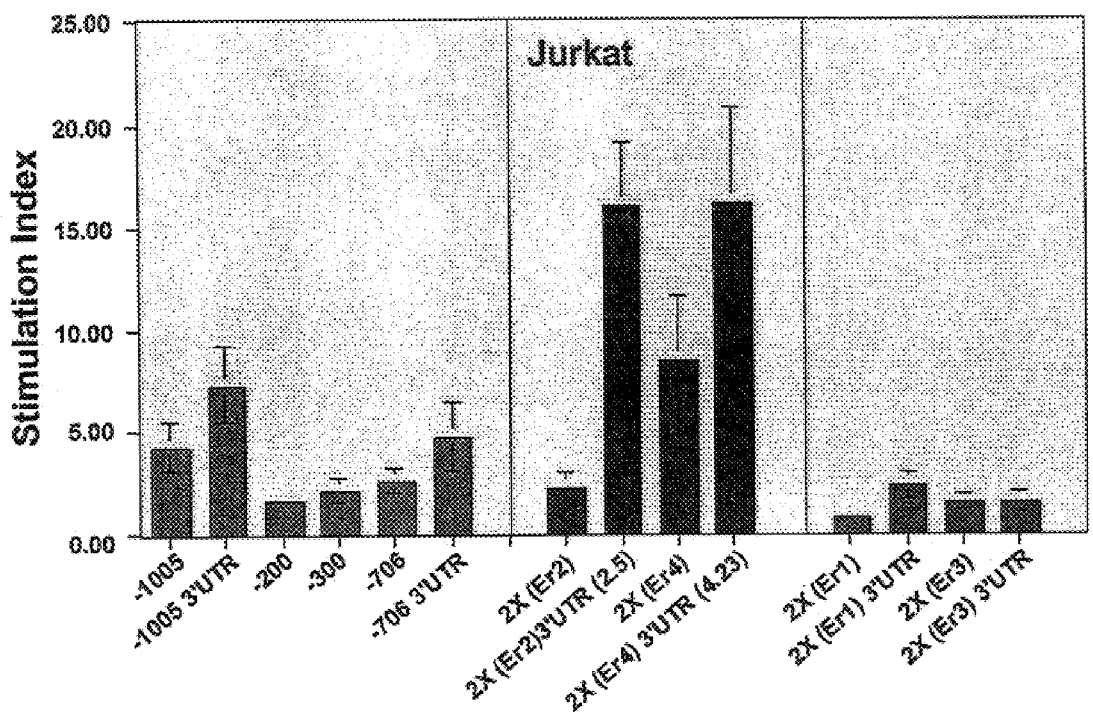
FIG. 11(b) shows results of experiments performed to assess expression of luciferase gene driven by the native −120 TNFα promoter, to which two copies of enhancer regions ER1, ER2, ER3 and ER4 are attached at the 5'end. The construct driving expression of the luciferase gene were in transiently transfected Jurkat Cells. Histograms represent stimulation index as a measure of inducibility by activating agent PMA. Jurkat cells produce TNFα following stimulation with PMA.
Figure 11C:
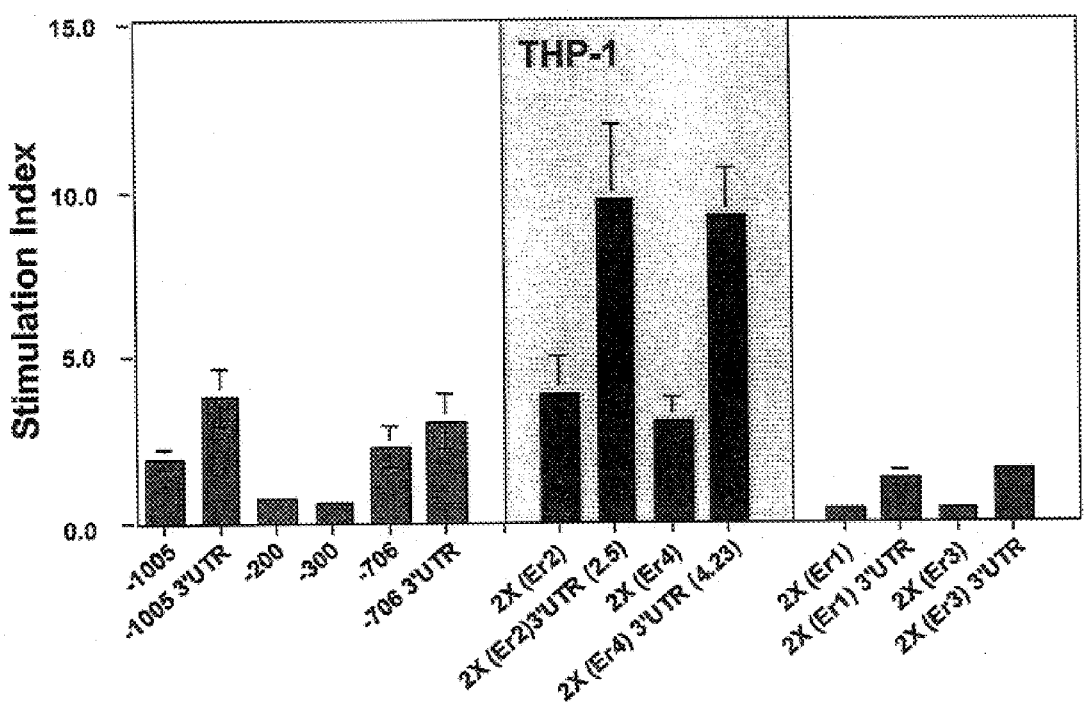
FIG. 11(c) shows results of experiments performed to assess expression of luciferase gene driven by the native −120 TNFα promoter, to which two copies of enhancer regions ER1, ER2, ER3 and ER4 are attached at the 5'end. The construct driving expression of the luciferase gene were in transiently transfected THP-1 Cells. Histograms represent stimulation index as a measure of inducibility by activating agent LPS. THP-1 cells produce TNFα following stimulation with LPS.

Genetic constructs were made in which the entire 3' untranslated region (SEQ ID NO: 13) was inserted downstream of the luciferase gene driven by deletion fragments, viz., −120, −706 and −1005 of the TNFα promoter. The results of the transient expression of these constructs are summarized in FIG. 9. Using the strategy, 3'UTR was also inserted downstream of Granzyme B the TNFpGB chimeric construct (FIGS. 6(*a*), 6(*b*), 12, and 13).

Example 2

Testing Protocols

In Vitro Methods:

Luciferase assay: Luciferase activity was determined using commercially available reagents (Promega).

Granzyme B gene expression:

a) Western blots of the transfected cell lysates were developed using anti-Granzyme B antibody.

b) Apoptosis of transfected cells: Apoptosis of transfected cells due to Granzyme B was determined by staining nuclei by propidium iodide (Krishan, A., J. Cell Biol., 66, 1994, 188–193) and by commercially available Cell Death ELISA kit (Boehringer Mannheim).

Animal Models

Rabbit model of IL-1β-induced arthritis (Pettipher E. R., et al., *Proc. Natl. Acad. Sci.*, 1986, 83, 8749–8753): IL-1β was injected into the knee joints of New Zealand White rabbits. Intra-articular injection of IL-1β causes dose-dependent infiltration of leukocytes into the joint space and loss of proteoglycan from the articular cartilage.

Antigen-Induced arthritis: Intra-articular injection of antigen (ovalbumin) into knee joints induces leukocyte accumulation and cartilage degradation that closely resembles rheumatoid arthritis in humans. The joint swelling following the injection was sustained for 14 days.

Scid mice-human synoviocytes model (Houri J. M., et al. *Current Opinions in Rheumatol.*, 1995, 7, 201–205; Sack U., et al., *J. Autoimmunity*, 1995, 9, 51–58; Geiler T., et al. *Arthritis & Rheumatism*, 1994, 37, 1664–1671): These were recently developed models for arthritis in which fresh synovial tissue from RA patients was implanted with normal human cartilage into scid mice either subcutaneously, under the renal capsule (Geiler T., et al., *Arthritis & Rheumatism*, 1994, 37, 1664–1671), or into knee joints (Sack U., et al., *J. Autoimmunity*, 1995, 9, 51–58). The implants grow with arthritis-like characteristics, including formation of pannus tissue of high cellular density, bone and cartilage erosion, development of multinuclear giant cells, and invasion of cartilage by synovial fibroblasts.

Indirect Method: Synoviocytes were transfected in vitro with the therapeutic gene and transplanted back in rabbits. Arthritis was induced in these rabbits by injecting IL-1β and expression of the therapeutic gene following activation was assessed. Activation-induced expression of the chimeric nucleic acid induces apoptosis in transplanted cells.

Direct Method: Intra-articular injection of the chimeric nucleic acids. Any of the gene delivery methods described above, including naked plasmid DNA, cationic liposome-mediated delivery can be used. For use of viral vector-based delivery, chimeric nucleic acids were cloned in suitable vectors. The vectors were then modified by deleting eukaryotic promoter present in these vectors. Intra-articular injection of the therapeutic genes inserted in appropriate vectors can then be done to assess therapeutic as well as prophylactic efficacy.

Example 3

Selection of TNFα Non-Producer Somatic Cell Variants

Cells (THP-1, Jurkat) were stably transfected in vitro with TNFp-AIG chimeric nucleic acid. After several cycles of stimulation, which induces apoptosis in the cells expressing the TNFp-AIG gene, surviving cells were then collected. A cDNA library from these cells was constructed, which was used for functional cloning (Legerski R and Peterson C., *Nature*, 1992, 359, 70–73; Jaattela M., et al., *Oncogene*, 1995, 10, 2297–2305).

Example 4

Identification and Characterization of Dominant Negative (DN) Genes

THP-1 and Jurkat cells stably transfected with TNFp-AIG were subjected to repeated cycles of stimulation to activate expression of TNFp-AIG. The cells, which do not express negative regulatory genes, undergo apoptosis, whereas those expressing dominant negative genes survive. In these surviving cells DN gene products act in-trans with the TNFα promoter, thereby inhibiting its activations to transcribe AIG, ultimately resulting in survival phenotype. cDNA library was constructed using polyadenylated mRNA from these cells. The DN genes which rescue TNFp-AIG-transfected THP-1 or Jurkat cells from apoptosis were identified by functional cloning as described for other genes (Legerski R. and Peterson C., *Nature*, 1992, 359, 70–73; Jaattela M., et al., *Oncogene*, 1995, 10, 2297–2305).

The above description was for the purpose of teaching the person of ordinary skill in the art how to practice the present invention, and it was not intended to detail all those obvious modifications and variations of it which will become apparent to the skilled worker upon reading the description. It was intended, however, that all such obvious modifications and variations be included within the scope of the present invention, which was defined by the following claims. The claims are intended to cover the claimed components and steps in any sequence which was effective to meet the objectives there intended, unless the context specifically indicates the contrary.

The papers cited herein are expressly incorporated in their entireties by reference.

What is claimed is:

1. A chimeric nucleic acid molecule comprising:
    at least one TNFα promoter enhancer region attached to a TNFα promoter, the enhancer region comprising the nucleic acid SEQ ID NO: 4, SEQ ID NO: 5, SEQ ID NO: 11, or SEQ ID NO: 12;
    the TNFα promoter further being attached to a nucleic acid sequence encoding the Granzyme B protein which in turn is further attached to a 3'UTR nucleic acid sequence.

2. The chimeric nucleic acid molecule according to claim 1 wherein there is present two to five TNFα promoter enhancer regions, and wherein any of the enhancer regions comprise SEQ ID NO: 5, SEQ ID NO: 12 or combinations thereof.

3. The chimeric nucleic acid molecule according to claim 2 wherein the TNFα promoter comprises the nucleic acid SEQ ID NO: 1, SEQ ID NO: 2, or SEQ ID NO: 3.

4. The chimeric nucleic acid molecule according to claim 1 wherein the nucleic acid molecule sequence is selected from the group consisting of SEQ ID NO: 13 and SEQ ID NO: 14.

5. The chimeric nucleic acid molecule according to claim 1 wherein the 3'UTR is ligated downstream of the Granzyme B nucleic acid sequence.

6. A process for constructing a chimeric nucleic acid molecule comprising at least one TNFα promoter enhancer attached to a functional copy of a minimal TNFα promoter attached to at least one copy of a functional apoptosis-inducing nucleic acid molecule which is further attached to a TNFα-3'UTR nucleic acid sequence, wherein the expression of the apoptosis-inducing nucleic acid is driven by the TNFα promoter comprising the steps of:
    (a) amplifying a nucleic acid molecule comprising a TNFα promoter by a polymerase chain reaction using primers which facilitate amplification of a desired TNF promoter construct;

(b) cloning the PCR-amplified nucleic acid obtained in step (a) upstream of a reporter nucleic acid sequence to produce constructs;

(c) testing the constructs obtained in step (b) for their constitutive and inducible expression in at least one TNFα-producing cell line;

(d) selecting a TNFα promoter responsible for inducible expression of the reporter in the cell line;

(e) PCR-amplifying TNFα promoter regions that enhance expression of the reporter to obtain an enhancer and ligating at least one copy of the enhancer upstream of the promoter of step (d);

(f) inserting at least one copy of a apoptosis-inducing nucleic acid molecule downstream of the TNFα promoter by replacing the reporter with the apoptosis-inducing nucleic acid deletion constructs, wherein the apoptosis-inducing nucleic acid encodes Granzyme B; and, (g) PCR-amplifying a TNFα-3UTR and ligating downstream of the apoptosis-inducing nucleic acid molecule to obtain the chimeric nucleic acid molecule.

7. The process according to claim 6 wherein two or more copies of the enhancer are inserted upstream of the promoter.

8. The process according to claim 6 wherein the reporter nucleic acid sequence encodes luciferase.

9. The process according to claim 6 wherein the enhancer comprises a sequence selected from the group consisting of SEQ ID NO: 4, SEQ ID NO: 5, SEQ ID NO: 11 and SEQ ID NO: 12.

10. The process according to claim 6 producing a chimeric nucleic acid molecule selected from the group consisting of SEQ ID NO: 13 and SEQ ID NO: 14.

11. The process according to claim 6 wherein the cell lines for testing constructs are selected from the group consisting of T lymphoblastoid, myelomonocytic, monocytic, fibroblast, cultured human synoviocytes and primary cells residing in RA.

* * * * *